US011753447B2

(12) United States Patent
Kreutzer et al.

(10) Patent No.: US 11,753,447 B2
(45) Date of Patent: Sep. 12, 2023

(54) CYCLIC PEPTIDES, METHODS OF SYNTHESIS, AND METHODS OF TREATMENT

(71) Applicant: The Regents of the University of California, Oakland, CA (US)

(72) Inventors: Adam G. Kreutzer, Irvine, CA (US); James S. Nowick, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/390,383

(22) Filed: Jul. 30, 2021

(65) Prior Publication Data
US 2022/0033444 A1  Feb. 3, 2022

Related U.S. Application Data

(60) Provisional application No. 63/059,904, filed on Jul. 31, 2020.

(51) Int. Cl.
*C07K 7/64* (2006.01)
*A61K 38/00* (2006.01)

(52) U.S. Cl.
CPC .............. *C07K 7/64* (2013.01); *A61K 38/00* (2013.01)

(58) Field of Classification Search
CPC ................................ C07K 7/64; A61K 38/00
See application file for complete search history.

(56) References Cited

FOREIGN PATENT DOCUMENTS

WO    WO 2019/048634    *   3/2019   .............. C07K 7/06

OTHER PUBLICATIONS

Khalily et al., 2018, Structure-based design, synthesis and anticancer effect of cyclic Smac-polyarginine peptides, Amino Acids, 50: 1607-1616.*
Koizumi et al., 2016, Structure-activity relationship of cyclic pentapeptide malformins as fibrinolysis enhancers, Bioorganic & Medicinal Chemistry Letters, 26: 5267-5271.*
Arosio et al., 2008, A Potent Integrin Antagonist from a Small Library of Cyclic RGD Pentapeptide Mimics Including Benzyl-Substituted Azabicycloalkane Amino Acids, ChemMedChem, 3: 1589-1603.*
Anand et al., "Coronavirus Main Proteinase (3CLpro) Structure: Basis for Design of Anti-SARS Drugs", Science, vol. 300, No. 5626, Jun. 13, 2003, pp. 1763-1767, doi: 10.1126/science.1085658.
Cohen et al., "Combination Prevention for COVID-19", Science, vol. 368, No. 6491, May 8, 2020, pp. 551, doi: 10.1126/science.abc5798.
Cross et al., "Sequence Characterization and Molecular Modeling of Clinically Relevant Variants of the SARS-CoV-2 Main Protease", Biochemistry, vol. 59, No. 39, Sep. 15, 2020, pp. 3741-3756, https://doi.org/10.1021/acs.biochem.0c00462.
Dai et al., "Structure-based design of antiviral drug candidates targeting the SARS-CoV-2 main protease", Science, vol. 368, No. 6497, Jun. 19, 2020, pp. 1331-1335, doi: 10.1126/science.abb4489.
Hegyi et al., "Conservation of substrate specificities among coronavirus main proteases", Journal of General Virology, vol. 83, No. 3, Mar. 2002, pp. 595-599, doi: https://doi.org/10.1099/0022-1317-83-3-595.
Hilgenfeld, "From SARS to MERS: crystallographic studies on coronaviral proteases enable antiviral drug design", The FEBS Journal, vol. 281, No. 18, Sep. 2014, Electronic Publication: Jul. 17, 2014, pp. 4085-4096.
Jin et al., "Structure of Mpro from SARS-CoV-2 and discovery of its inhibitors", Nature, vol. 582, Jun. 11, 2020, pp. 289-293.
Trott et al., "AutoDock Vina: improving the speed and accuracy of docking with a new scoring function, efficient optimization, and multithreading", Journal of Comput. Chem., Jan. 30, 2010, vol. 31, No. 2, pp. 455-461, doi: 10.1002/jcc.21334.
Vanommeslaeghe et al., "Automation of the CHARMM General Force Field (CGenFF) I: Bond Perception and Atom Typing", Journal of Chemical Information and Modeling, vol. 52, No. 12, Nov. 12, 2012, pp. 3144-3154, https://doi.org/10.1021/ci300363c.
Vanommeslaeghe et al., "Automation of the CHARMM General Force Field (CGenFF) II: Assignment of Bonded Parameters and Partial Atomic Charges", Journal of Chemical Information and Modeling, vol. 52, No. 12, Nov. 12, 2012, pp. 3155-3168, https://doi.org/10.1021/ci3003649.
Vinogradov et al., "Macrocyclic Peptides as Drug Candidates: Recent Progress and Remaining Challenges", Journal of the American Chemical Society, vol. 141, No. 10, Feb. 15, 2019, pp. 4167-4181, doi: https://doi.org/10.1021/jacs.8b13178.
Xue et al., "Structures of Two Coronavirus Main Proteases: Implications for Substrate Binding and Antiviral Drug Design", Journal of Virology, vol. 82, No. 5, Mar. 2008, pp. 2515-2527, doi: https://doi.org/10.1128/JVI.02114-07.
Zhang et al., "Crystal structure of SARS-CoV-2 main protease provides a basis for design of improved α-ketoamide inhibitors", Science, vol. 368, No. 6489, Apr. 24, 2020, pp. 409-412, doi: 10.1126/science.abb3405.
Zhang et al., "α-Ketoamides as Broad-Spectrum Inhibitors of Coronavirus and Enterovirus Replication: Structure-Based Design, Synthesis, and Activity Assessment", Journal of Medicinal Chemistry, vol. 63, No. 9, Feb. 11, 2020, pp. 4562-4578, doi: https://doi.org/10.1021/acs.jmedchem.9b01828.

* cited by examiner

*Primary Examiner* — Amber D Steele
(74) *Attorney, Agent, or Firm* — KPPB LLP

(57) ABSTRACT

Cyclic peptide compounds and methods of their synthesis are provided. Formulations and medicaments are also provided that are directed to the treatment of coronavirus. Therapeutics are also provided containing a therapeutically effective dose of one or more cyclic peptide compounds, present either as pharmaceutically effective salt or in pure form, including, but not limited to, formulations for oral, intravenous, or pulmonary administration.

25 Claims, 14 Drawing Sheets
Specification includes a Sequence Listing.

m = 1 to 4
n = 5 to 50

[4-(2-aminoethyl)phenyl]-acetic acid

[3-(2-aminoethyl)phenyl]-acetic acid 2-(5-(2-aminoethyl)furan-2-yl)acetic acid 2-(5-(2-aminoethyl)thiophen-2-yl)acetic acid 2-(5-(2-aminoethyl)-1H-pyrrol-2-yl)acetic acid 6-aminohexanoic acid 7-aminoheptanoic acid 8-aminooctanoic acid 9-aminononanoic acid Laa is a linker amino acid

| P2 | |
|---|---|
| unbranched and beta branched amino acids | substituted phenylalanine derivatives |
|  e.g. R or R' = H, CH$_3$, CH$_2$CH$_3$, CH$_2$(CH$_3$)$_2$ (CH$_3$)$_2$, (CH$_3$)$_3$, cyclopropyl |  e.g. R or R' = H, CH$_3$, CH$_2$CH$_3$, CH$_2$(CH$_3$)$_2$, phenyl, benzoyl, pyridyl, acetyl, halogen |

P3'

R1–R5 = H, Me

UCI-1　　Seq. ID No. 58 peptide-1a
Seq. ID No. 58 peptide-1b
Seq. ID No. 58 peptide-1c tri-Ala-UCI-1

CYCLIC PEPTIDES, METHODS OF SYNTHESIS, AND METHODS OF TREATMENT

CROSS REFERENCE TO RELATED APPLICATIONS

This application claims priority to U.S. Provisional Application Ser. No. 63/059,904 entitled "Cyclic Peptides, Methods of Synthesis, and Methods of Treatment," filed Jul. 31, 2020, which is herein incorporated by reference in its entirety.

SEQUENCE LISTING

The instant application contains a Sequence Listing which has been submitted electronically in ASCII format and is hereby incorporated by reference in its entirety. The ASCII copy was created on Jul. 29, 2021, is named R1-06797_SL.txt, and is 22,793 bytes in size.

TECHNICAL FIELD

Embodiments are generally directed to synthetic cyclic peptides, which may be used for inhibiting viral enzymes, methods of synthesis of these molecules, and methods for the treatment of utilizing these molecules.

BACKGROUND

Peptides are short protein polymers formed of amino acids chained together via a backbone. Accordingly, in standard peptide conformations, each amino acid of the polymer is linked via an Amine ($NH_2$)-Carbon (C)-Carboxylic Acid (COOH) backbone. Each amino acid is defined by a side chain that extends from the carbon of the backbone. There are about five hundred naturally occurring amino acids, but only twenty standard amino acids that appear in the genetic code (i.e., DNA encodes proteins and peptides utilizing 20 amino acids).

Peptides are typically linear polymers, meaning that the backbone has two terminal points, which are referred to the N-terminus (amino terminal point) and C-terminus (carboxyl terminal point). Cyclic peptides, however, do exist in nature and require a linkage. Various linkages exist in nature, including direct amide linkage (i.e., amide linkage between N-terminus and C-terminus), non-alpha amide linkage (e.g., amide linkage between C-terminus and an amino group of an amino acid side chain), ester linkage (e.g., ester linkage between C-terminus and a hydroxyl group of an amino acid side chain), and bridging linkage (i.e., a linkage between two amino acid side chains, especially disulfide linkages between cysteine side chains).

SUMMARY

Several embodiments are directed towards cyclic peptides having an amino acid linker and synthesis of cyclic peptides. Numerous embodiments are also directed towards methods of treating a subject with a cyclic peptide, especially for the treatment of coronavirus infection.

In an embodiment, a cyclic peptide comprises three or more amino acids. A first amino acid of the cyclic peptide is a linker. The linker comprises a first amide group and a first carbonyl group. The first amide group is in an amide bond with a second carbonyl group a second amino acid of the cyclic peptide and the first carbonyl group is in an amide bond with a second amide group with a third amino acid of the cyclic peptide. The first amide group is 5, 6, 7 or 8 atoms apart from the first carbonyl group. In some instances, the linker comprises a planar cyclic group. In some instances, the linker comprises five or six atoms in a single plane. In some instances, the cyclic peptide is a pentapeptide.

In an embodiment is a cyclic peptide having the following formula:

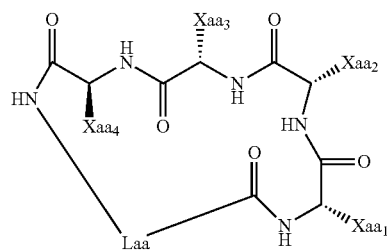

$Xaa_1$ is a hydrophobic amino acid. $Xaa_2$ is an amino acid capable of hydrogen bonding. $Xaa_3$ is any amino acid. $Xaa_4$ is any amino acid. Laa is a linker amino acid, and the linker amino acid is [3-(2-aminoethyl)phenyl]-acetic acid, [4-(2-aminoethyl)phenyl]-acetic acid, 2-(5-(2-aminoethyl)furan-2-yl)acetic acid, 2-(5-(2-aminoethyl)thiophen-2-yl)acetic acid, 2-(5-(2-aminoethyl)-1H-pyrrol-2-yl)acetic acid, 6-aminohexanoic acid, 7-aminoheptanoic acid, 8-aminooctanoic acid, or 9-aminononanoic acid. In some instances, $Xaa_1$ is Phe, d-Phe, homo-Phe, Leu, d-Leu, or Cha. In some instances, $Xaa_2$ is Gln or γ-lactam Gln. In some instances, $Xaa_3$ is Gly, Ser, Ala, Asn, Phe, Trp, phenylglycine Thr, or allo-Thr. In some instances, $Xaa_4$ is Lys, Gly, Ala, Val, or Leu. In some instance, the cyclic peptide is a therapeutic. In some instance, the cyclic peptide is an antiviral.

In an embodiment, a subject is administered as a course of treatment an effective amount of a cyclic peptide of formula:

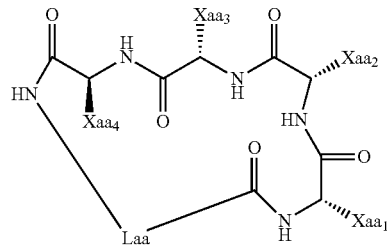

$Xaa_1$ is a hydrophobic amino acid. $Xaa_2$ is an amino acid capable of hydrogen bonding. $Xaa_3$ is any amino acid. $Xaa_4$ is any amino acid. Laa is a linker amino acid, and the linker amino acid is [[3-(2-aminoethyl)phenyl]-acetic acid, [4-(2-aminoethyl)phenyl]-acetic acid, 2-(5-(2-aminoethyl)furan-2-yl)acetic acid, 2-(5-(2-aminoethyl)thiophen-2-yl)acetic acid, 2-(5-(2-aminoethyl)-1H-pyrrol-2-yl)acetic acid, 6-aminohexanoic acid, 7-aminoheptanoic acid, 8-aminooctanoic acid, or 9-aminononanoic acid. In some instances, $Xaa_1$ is Phe, d-Phe, homo-Phe, Leu, d-Leu, or Cha. In some instances, $Xaa_2$ is Gln or γ-lactam Gln. In some instances, $Xaa_3$ is Gly, Ser, Ala, Asn, Phe, Trp, phenylglycine Thr, or allo-Thr. In some instances, $Xaa_4$ is Lys, Gly, Ala, Val, or Leu. In some instances, the subject is infected with coronavirus. In some instances, the compound is administered to the subject to prophylactically treat an infection of coronavirus. In some instances, the subject is an animal, a mammal, a bird, a reptile, a primate, a human, a pet, a farm animal, or a zoo animal.

BRIEF DESCRIPTION OF THE DRAWINGS

The description and claims will be more fully understood with reference to the following figures and data graphs, which are presented as exemplary embodiments of the disclosure and should not be construed as a complete recitation of the scope of the disclosure.

FIG. 17A provides LC/MS total ion current spectrum of well solution from $M^{pro}$ inhibition assay with 187.5 μM UCI-1. FIG. 17B provides LC/MS total ion current spectrum of well solution from $M^{pro}$ inhibition assay with 187.5 μM UCI-1 spiked with 0.2 μM peptide-1c. FIG. 17C provides ion current for peptide-1c (2.2 min) in LC/MS spectrum of well solution from $M^{pro}$ inhibition assay with 187.5 μM UCI-1. FIG. 17D provides ion current for peptide-1c (2.2 min) in LC/MS spectrum of well solution from $M^{pro}$ inhibition assay with 187.5 μM UCI-1 spiked with 0.2 μM peptide-1c.

DETAILED DESCRIPTION

Turning now to the drawings and data, cyclic peptides, methods of their synthesis, and methods of their use, in accordance with the various embodiments, are described. In several embodiments, a cyclic peptide incorporates a linker, which is used to link the termini of a linear peptide into a cyclic molecule. In some embodiments, a linker is one or more amino acids having available carbonyl and amide groups for linking, such that the carbonyl and amino groups flanking the linker are 5, 6, 7, or 8 atoms apart in the resulting cyclic peptide. In some embodiments, a linker is a molecule having a planar cyclic group (e.g., benzene, pyrrole, furan or thiophene), which can stabilize a cyclic peptide into a more rigid structure. In some embodiments, a linker is an amino acid molecule comprising an extension of five or six atoms in a single plane, such as linkers having a phenyl, a pyrrolyl, a furyl, or a thienyl entity. In various embodiments, a cyclic peptide having an amino acid linker further incorporates two or more amino acids with the linker to formulate the cyclic macromolecule. In some embodiments, a linear peptide with the linker molecule as the C-terminal amino acid is cyclized via a carbonyl substitution reaction with a free carboxyl of a linker molecule and the amino group of an N-terminal amino acid.

Various embodiments are directed to cyclic peptides for inhibition of various proteases. In some embodiments, cyclic peptides incorporate amino acids to fit within an enzyme active site to inhibit the enzyme. In some embodiments, a cyclic peptide is designed to fit within the coronavirus M protease ($M^{pro}$) active site. Further, various embodiments are directed to the use of a cyclic peptide as a treatment for coronavirus infection.

Cyclic Peptides Utilizing an Amino Acid Linker

Figure 1A:
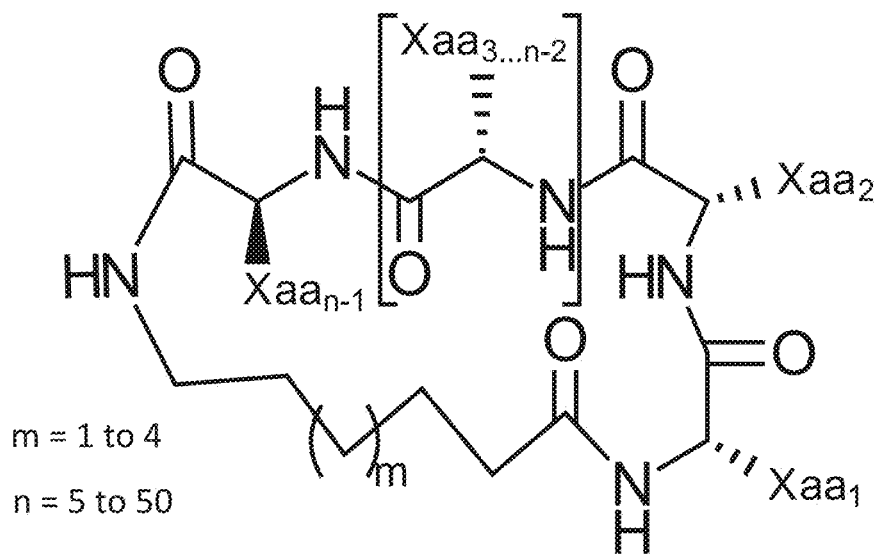
FIG. 1A provides a molecular structure diagram of a cyclic peptide utilizing an amino acid linker in accordance with various embodiments.
Figure 1B:
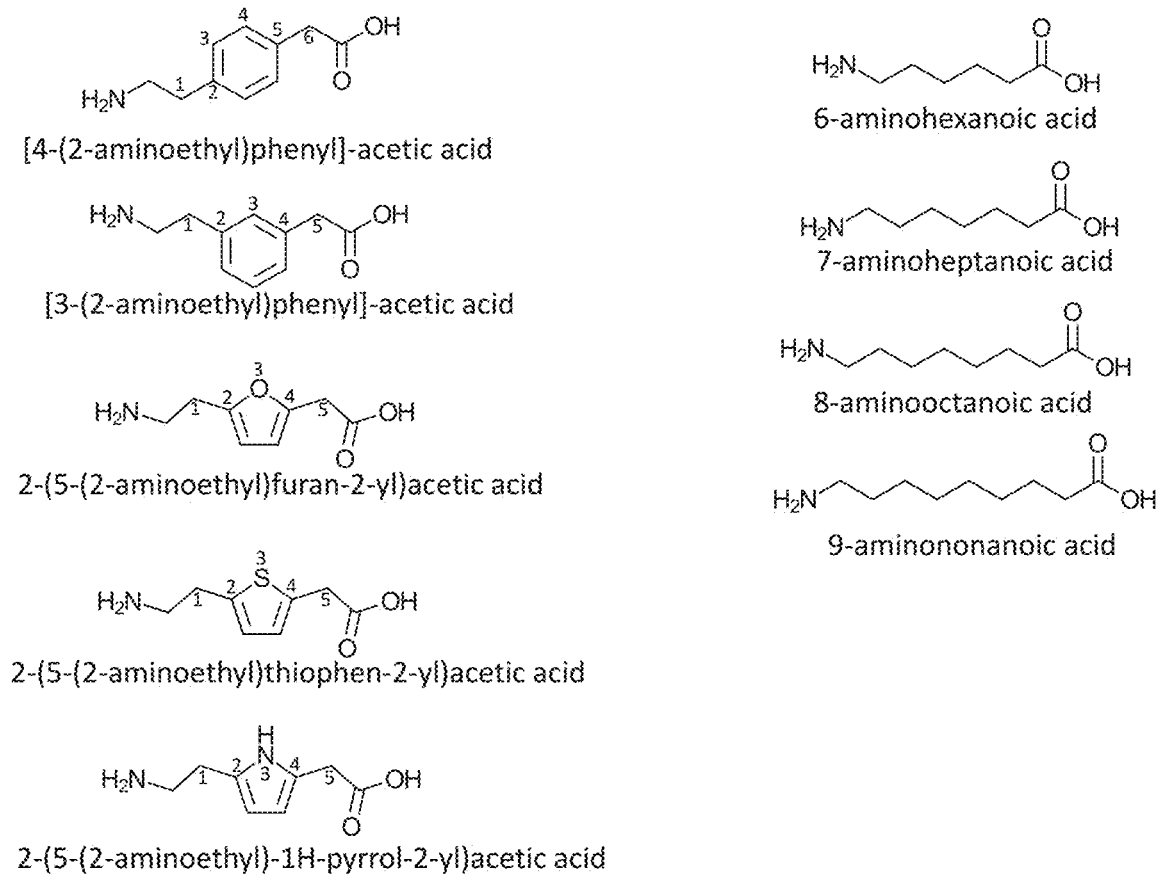
FIG. 1B provides molecular structures of various amino acids for use as a linker in accordance with various embodiments.

Compounds in accordance with various embodiments are based on cyclic peptides that incorporate an amino acid linker. Provided in FIG. 1A is an example of a cyclic peptide incorporating an amino acid linker, which provides linker function between the amino group of a first amino acid and the carboxyl group of the penultimate amino acid, the ultimate amino acid being the linker. Various embodiments are directed to a cyclic peptide having a minimum of five amino acids (including the linker), such as one shown in FIG. 1C. Any appropriate amino acid can be utilized as the linker. In some embodiments, a linker is one or more amino acids having available carboxy and amino groups for linking, such that the carbonyl and amino groups are 5, 6, 7, or 8 atoms apart in the resulting cyclic peptide (FIG. 1A). In various embodiments, a linker is [3-(2-aminoethyl)phenyl]-acetic acid, [4-(2-aminoethyl)phenyl]-acetic acid, 2-(5-(2-aminoethyl)furan-2-yl)acetic acid, 2-(5-(2-aminoethyl)thiophen-2-yl)acetic acid, 2-(5-(2-aminoethyl)-1H-pyrrol-2-yl) acetic acid, 6-aminohexanoic acid, 7-aminoheptanoic acid, 8-aminooctanoic acid, or 9-aminononanoic acid (FIG. 1B). In some embodiments, a linker is a molecule having a planar cyclic group (e.g., phenyl, pyrrole, furan, or thiophene), which can stabilize a cyclic peptide into a more rigid structure. In some embodiments, a linker is an amino acid molecule comprising an extension of five or six atoms in a single plane, such as linkers having a phenyl, a pyrrolic, a furanic, or a thienyl entity. For example, as shown in FIG. 1B, [4-(2-aminoethyl)phenyl]-acetic acid has six atoms and [3-(2-aminoethyl)phenyl]-acetic acid has five atoms in a single plane. Similarly, 2-(5-(2-aminoethyl)furan-2-yl)acetic acid, 2-(5-(2-aminoethyl)thiophen-2-yl)acetic acid, 2-(5-(2-aminoethyl)-1H-pyrrol-2-yl)acetic acid each have five atoms in a single plane. In some embodiments, a carbon atom of linker is exchanged with another organic atom. An example of an exchange is formation of pyridine ring by exchanging one or more carbon atoms with nitrogen atoms. In some embodiments, a linker is further substituted on any of its organic atoms.

Figure 1C:
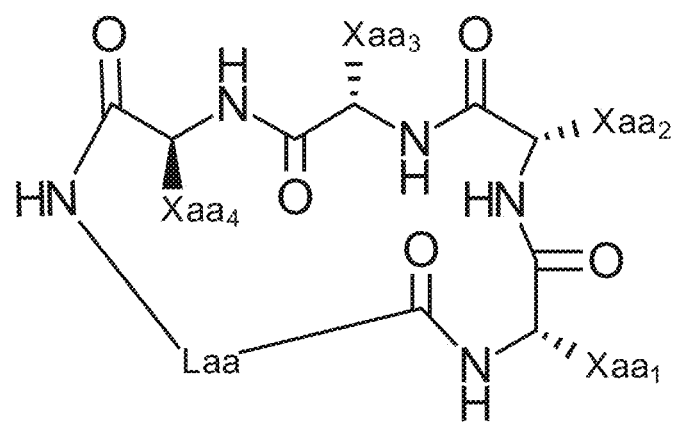
FIG. 1C provides a molecular structure diagram of a cyclic pentapeptide utilizing an amino acid linker in accordance with various embodiments.

As can be seen in FIGS. 1A and 1C, any appropriate amino acid can be incorporated within the cyclic peptide. Further, a cyclic peptide with an amino acid linker can incorporate any appropriate number of amino acids, which is depicted in FIG. 1A with squared brackets to signify polymeric extension of internal amino acids. In various embodiments, a cyclic peptide with an amino acid linker incorporates any whole number between 3 and 50, or more, amino acids, inclusive of the linker amino acid. In various embodiments, a cyclic peptide with an amino acid linker incorporates 3, 4, 5, 6, 7, 8, 9, 10, 11, 12, 13, 14, 15, 16, 17, 18, 19, 20, 25, 30, 35, 40, 45, or 50 amino acids.

In many embodiments, a cyclic peptide is synthesized first as a linear peptide utilizing solid-phase peptide synthesis (SPPS). Any appropriate SPPS protocol can be utilized. The solid support can be any appropriate solid support, such as (for example) the Merrifield resin, the PAM resin, the Wang resin, or 2-chlorotrityl resin. Any appropriate protecting groups can be utilized, such as (for example) Fmoc or Boc.

Peptides are generally synthesized in reverse order as compared to natural synthesis via ribosomes. In other words, synthetic peptides are generally synthesized from the C-terminus to the N-terminus. Accordingly, in many embodiments, a linear peptide is synthesized with a linker amino as the C-terminal amino acid. In various embodiments, the linker amino acid comprises an available carboxyl group five to eight atoms away from an amino group. Once the full linear peptide is synthesized and released from the solid support, the linear peptide is cyclized utilizing a carbonyl substitution reaction between the free carboxyl group of the linker molecule and the free amino group of the N-terminal amino acid, resulting in a carbonyl-amide linkage (See FIGS. 1A and 1C).

Cyclic peptides can be designed with an amino acid sequence to fit within a site of an enzyme (e.g., active site) to affect an action upon that enzyme (e.g., inhibition). Accordingly, in some embodiments, amino acids are selected that mimic an enzyme's natural substrate. In some embodiments, amino acids are selected that enhance the ability to bind within the enzyme site, as compared to the ability of a natural substrate. In some embodiments, amino acids are selected to perform a specific task (e.g., transform the enzyme into a particular conformation). Further, in some embodiments, a cyclic peptide is substituted in various ways to enhance the peptide. In some embodiments, a cyclic peptide is substituted to increase interaction with the enzyme site. In some embodiments, a cyclic peptide is substituted to enhance the peptide stability and/or conformation. In some embodiments, a cyclic peptide is substituted to enhance the peptide's medicinal function, such as (for example) increasing solubility, increasing bioavailability, increasing cellular uptake, decreasing cytotoxicity, and/or decreasing hemolysis. In some embodiments, cellular uptake is increased with N-methyl substitutions on amino groups of the amide backbone of a cyclic peptide. In some embodiments, cellular uptake is increased with cell-penetrating peptides (CPPs) incorporated within or extended from a residue of a cyclic peptide. In some embodiments, poly-Arg is utilized a CPP.

Cyclic Peptides for Coronavirus M Protease

Several embodiments are directed towards the use of cyclic peptides with an amino acid linker to inhibit the M protease of Coronavirus (CoV) family, including (but not limited to) human coronavirus (hCoV), murine coronavirus (MuCoV), and any other zoonotic coronavirus. The M protease ($M^{pro}$) is the principal protease of coronavirus that cleaves the various peptide products of the coronavirus genome into functional proteins for viral replication and packaging. Accordingly, inhibiting $M^{pro}$ provides an ability to treat and/or prevent various diseases related to coronavirus infection, including (but not limited to) severe acute respiratory syndrome (SARS), middle east respiratory syndrome (MERS), coronavirus disease 2019 (COVID-19), multisystem inflammatory syndrome in children (MIS-C) and the common cold. Furthermore, $M^{pro}$ is highly conserved amount the various strains of coronavirus. Thus, cyclic peptides that are functional against one strain of $M^{pro}$ would be expected to be effective against other strains. In other words, cyclic peptides described herein are expected to be effective against any coronavirus strain, past, present or future, and of any zoonotic origin.

Figure 2:
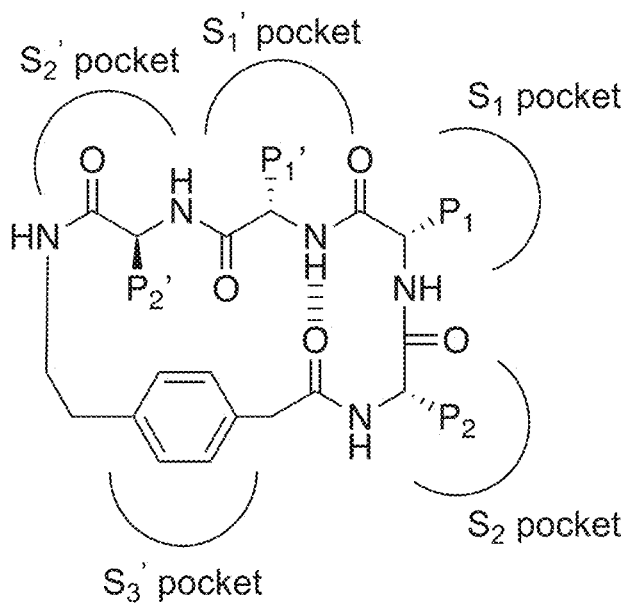
FIG. 2 provides a molecular structure diagram of a cyclic pentapeptide fitting within the pockets of the coronavirus M protease in accordance with various embodiments.
Figure 3:
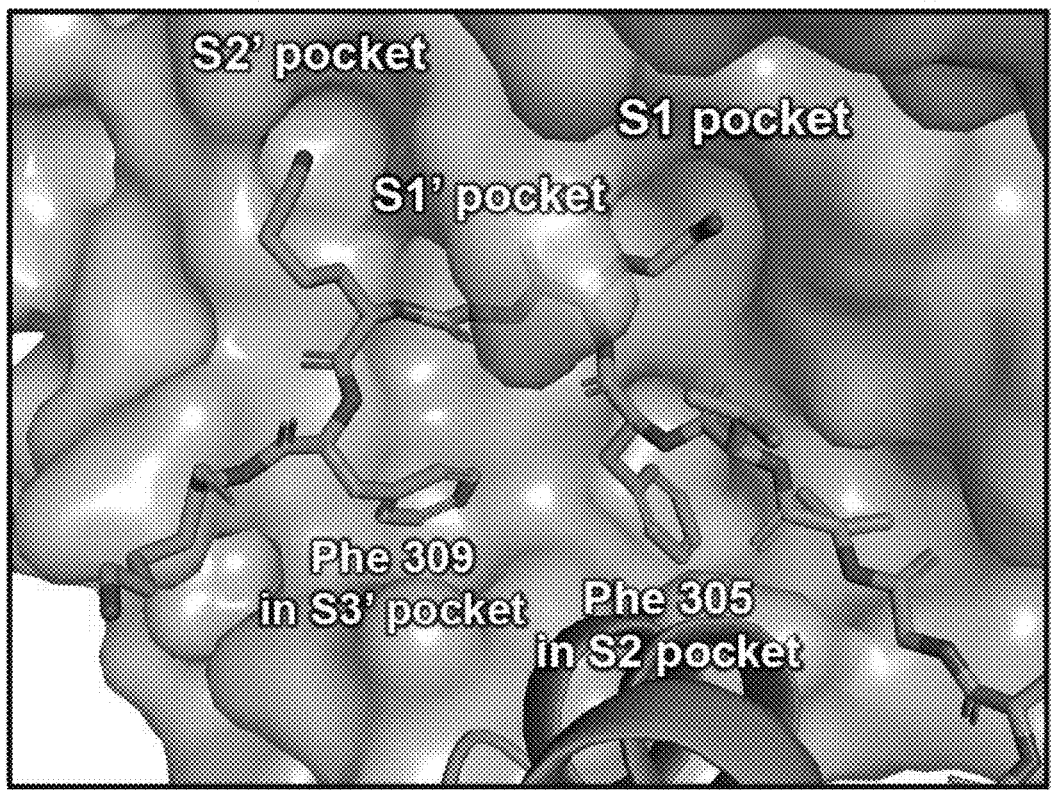
FIG. 3 provides a crystallographic image of the C-terminal autolytic cleavage site substrate within the active site of the coronavirus M protease in accordance with various embodiments.

Provided in FIG. 2 is a depiction of an embodiment of a pentapeptide for fitting within the $M^{pro}$ active site, which includes various pockets named $S_1$, $S_2$, $S_1'$, and $S_3'$. In several embodiments, the $P_2$, $P_1$, $P_1'$, $P_2'$ and $P_3'$ amino acids are a mimic of the C-terminal autolytic cleavage site of $M^{pro}$, which are residues 305-309 and have the amino acid sequence FQGKF (SEQ. ID No. 1). Provided in FIG. 3 is crystallographic depiction of the $M^{pro}$ active site with the C-terminal autolytic cleavage site substrate. The Phe305 sits within the $S_2$ pocket, the Gln306 sits within the $S_1$ pocket, the Gly307 sits within the $S_1'$ pocket, the Lys308 sits within the $S_2'$ pocket, and the Phe309 sits within the $S_3'$ pocket. Accordingly, various amino acid surrogates that provide an ability to fit within the designated pockets of the $M^{pro}$ active site can be utilized in accordance with various embodiments.

In many embodiments, the $P_3'$ amino acid of the pentapeptide is utilized as a linker to cyclize the peptide. Any appropriate linker having an available carboxyl group as described herein can be utilized as a linker in a pentapeptide, such as those provided in FIG. 1B. In some embodiments, an amino acid with a planar ring is utilized as a linker. Examples amino acids with a planar ring include (but not limited to) [3-(2-aminoethyl)phenyl]-acetic acid, [4-(2-aminoethyl)phenyl]-acetic acid, 2-(5-(2-aminoethyl)furan-2-yl) acetic acid, 2-(5-(2-aminoethyl)thiophen-2-yl)acetic acid, and 2-(5-(2-aminoethyl)-1H-pyrrol-2-yl)acetic acid, each of which can be utilized as a linker to connect the $P_2'$ amino acid with the $P_2$ amino acid to cyclize the pentapeptide. In some embodiments, as shown in the depicted embodiment within FIG. 2, the carboxy terminus of the $P_2'$ residue is linked to the amino terminus of the $P_2$ residue via an aromatic group to form a cyclophane. Aromatic groups confer various advantages for use within a pentapeptide to fit within the $M^{pro}$ active site, such as (for example) including a planar and aromatic ring structure similar to the Phe309 of the native substrate. Further, when the $P_2$ and $P_1$ amino acids form a β-turn formation, the carbonyl of the aromatic amino acid can form a hydrogen bond with the amino group of $P_1$ (FIG. 2). Although a phenyl group is shown in FIG. 2, it should be understood that furyl, thienyl, pyrrolyl, or other appropriate aromatic groups can be utilized.

Various embodiments are directed towards various combinations of peptide sequences to yield a cyclic pentapeptide capable of fitting within the $M^{pro}$ active site. Accordingly, various embodiments incorporate a linker residue that is capable of siting within the $S_3'$ pocket, a $P_2'$ residue that is capable of siting within the $S_2'$ pocket, a $P_1'$ amino acid that is capable of siting within the $S_1'$ pocket, a $P_1$ amino acid that is capable of siting within the $S_1$ pocket, a $P_2$ amino acid that is capable of siting within the $S_2$ pocket, and $P_2$ and $P_1$ amino acids that form a β-turn formation. Table 1 provides various amino acids that can be utilized in a pentapeptide for fitting within the $M^{pro}$ active site. It is to be understood that any combination of listed amino acids can be utilized in a pentapeptide in accordance with various embodiments. Exemplary peptide sequences are provided as SEQ ID NOs: 2 to 55, which can be linked with any appropriate linker, such as the linkers described herein, in order to form a cyclic pentapeptide.

TABLE 1

Various Amino Acids for Use within Cyclic Pentapeptide for Coronavirus M protease

| Residue | Amino Acids |
| --- | --- |
| $P_2$ | Hydrophobic AA, Examples include (but are not limited to) Phe, d-Phe, homo-Phe, Leu, d-Leu, Cha |
| $P_1$ | AA with hydrogen bonding, Examples include (but are not limited to) Gln, γ-lactam Gln, other Gln analogues |
| $P_1'$ | Any AA, Examples include (but are not limited to) Gly, Ser, Ala, Asn, Phe, Trp, phenylglycine Thr, allo-Thr, Xaa |
| $P_2'$ | Any AA, Examples include (but are not limited to) Lys, Gly, Ala, Val, Leu, Xaa |
| Linker | AA with available carboxy group; Examples include (but are not limited to) [3-(2-aminoethyl)phenyl]-acetic acid, [4-(2-aminoethyl)phenyl]-acetic acid, [3-(2-aminoethyl)furyl]-acetic acid, [3-(2-aminoethyl)thienyl]-acetic acid, and [3-(2-aminoethyl)pyrrolyl]-acetic acid, 6-aminohexanoic acid, 7-aminoheptanoic acid, 8-aminooctanoic acid, 9-aminononanoic acid |

In regards to the $P_2$ position, previous inhibitor designs for $M^{pro}$ have shown that the $S_2$ pocket exhibits considerable plasticity, accommodating variably sized hydrophobic moieties. Accordingly, various embodiments are directed towards various use of hydrophobic amino acids in the $P_2$ position. In some embodiments, D-conformation of amino acids will be utilized (e.g., d-Phe, d-Leu) in the $P_2$ position. In some embodiments, cyclohexylalanine (Cha), homo-phenylalanine (homo-Phe), or leucine (Leu), will be utilized in the $P_2$ position. Notably, Leu is the most common amino acid at the $P_2$ position among the 11 native SARS-CoV-2 $M^{pro}$ cleavage sites. Modeling studies suggests that the $S_2$ pocket could accommodate any of the aforementioned amino acids.

In regards to the $P_1$ position, in accordance with various embodiments, an amino acid with hydrogen bonding capability is utilized. For example, a γ-lactam glutamine analog has proven to fill the S1 pocket well. Accordingly, in some embodiments, a γ-lactam Gln is utilized at the P1 position. Additional glutamine analogues can also be utilized.

In regards to the $P_1'$ position, the $S_1'$ pocket typically accommodates a small amino acid, such as glycine, alanine, serine, or asparagine, however, it has been demonstrated that the $S_1'$ pocket can also accommodate larger groups, such a phenyl groups and indole group as in phenylalanine, tryptophan, or phenylglycine. Further, based on modeling studies, it is noted that the P1' position is proximal to the side chain of Leu27, which creates a pocket that might accommodate a methyl group of threonine or allo-threonine. Accordingly, in various embodiments, Gly, Ala, Ser, Asn, Phe, Trp, or phenylglycine, Thr, or allo-Thr is utilized in the $P_1'$ position, however, many other amino acids can be accommodated and thus can be utilized in various embodiments.

In regards to the $P_2'$ position, The $S_2'$ pocket is also fairly plastic. Glycine and lysine are the most common amino acids at the $P_2'$ position among coronaviruses, however, many various amino acids can be incorporated. For example, modeling studies provide that alanine, valine, and leucine are accommodated at this position. Accordingly, in various embodiments, Gly, Lys, Ala, Val, Leu, or any amino acid (Xaa) is utilized in the $P_2'$ position.

Numerous embodiments are also directed to further substituting the amino acids of the cyclic pentapeptide. Any appropriate substituent may be utilized, especially substituents that provide an enhancement the peptide. In some embodiments, a cyclic peptide is substituted to increase interaction with the binding site. In some embodiments, a cyclic peptide is substituted to enhance the peptide stability and/or conformation. In some embodiments, a cyclic peptide is substituted to enhance the peptide medicinally, such as (for example) increasing solubility, increasing bioavailability, increasing cellular uptake, decreasing cytotoxicity, and/or decreasing hemolysis.

Figure 4:
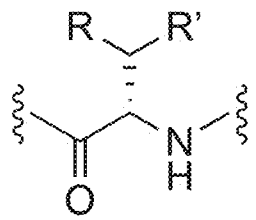
FIG. 4 provides a molecular structure diagram of substitutions on the $P_2$ residue in accordance with various embodiments.
Figure 4:
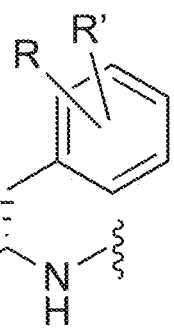

In regards to the $P_2$ residue, X-ray crystallography, molecular modeling, and SAR studies suggest that various substituents can be utilized. In some embodiments that utilize phenylalanine (e.g., l-Phe, d-Phe, homo-Phe) in $P_2$, the phenyl group can incorporate alkyl group substituents by (FIG. 4). Likewise, in some embodiments that utilized unbranched or beta branched amino acids, various alkyl substituents can be utilized (FIG. 4).

Figure 5:
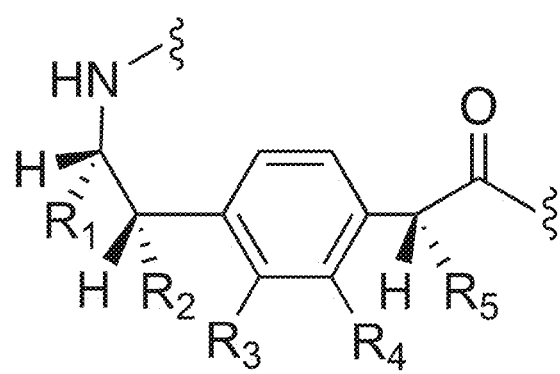
FIG. 5 provides a molecular structure diagram of substitutions on [4-(2-aminoethyl)phenyl]-acetic acid in accordance with various embodiments of the invention.

In regards to the $P_2'$ residue, various substituents can be added to optimize the binding of the $S_2'$ pocket and/or increase cell permeabilization. In addition, modeling studies indicate that the $P_3'$ pocket could accommodate methyl groups on the linker amino acid. Accordingly, in various embodiment, methyl substituents are incorporated on the methylene carbons and/or the aromatic ring, which may enhance the peptides interaction with the $S_3'$ pocket (FIG. 5). Notably, although a phenyl ring is shown, similar substitutions would be available on other planar cyclic groups.

Figure 6:
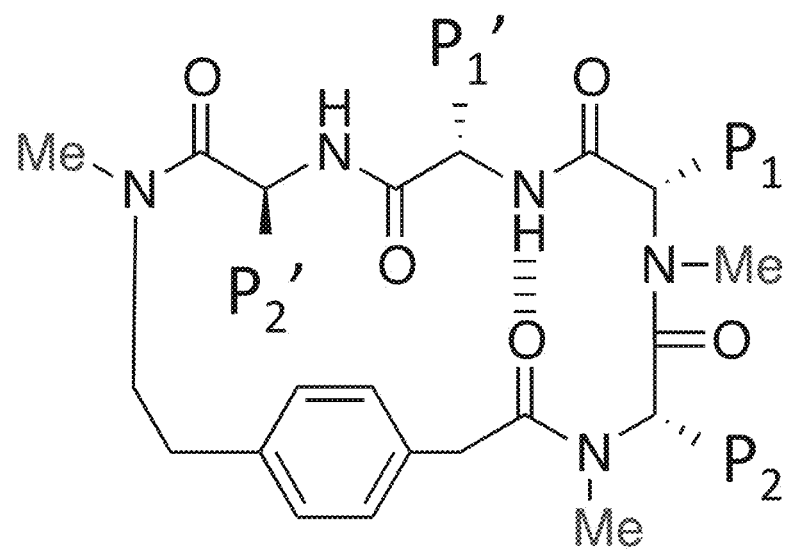
FIG. 6 provides a molecular structure diagram of a cyclic pentapeptide with N-methyl substituents on the amide backbone in accordance with various embodiments.

In some embodiments, one or more amino groups of the amide backbone of the cyclic pentapeptide with N-methyl substituents. In some embodiments, two or more amino groups of the amide backbone of the cyclic pentapeptide with N-methyl substituents. In some embodiments, three or one amino groups of the amide backbone of the cyclic pentapeptide with N-methyl substituents. In some embodiments, four or more amino groups of the amide backbone of the cyclic pentapeptide with N-methyl substituents. In some embodiments, all five amino groups of the amide backbone of the cyclic pentapeptide with N-methyl substituents. Provided in FIG. 6 is an example of the cyclic pentapeptide with three N-methyl substituents on the amino groups of the P3' (linker), P2, and P1 residues.

In some embodiments, the cyclic pentapeptide incorporates cell-penetrating peptides (CPPs) extended from a residue of a cyclic peptide. In some embodiments, poly-Arg is utilized a CPP. In some embodiments, a CPP is extended from the $P_2$ position. In some embodiments, a CPP is extended from the $P_2'$ position.

Modes of Treatment

Several embodiments are directed to the use of cyclic peptides (especially cyclic pentapeptides) as a therapeutic. In some embodiments, cyclic peptides are administered in a therapeutically effective amount to a subject as part of a course of treatment. Subjects include any animal, including (but not limited to) an animal, a mammal, a bird, a reptile, a primate, a human, a pet, a farm animal, or a zoo animal. As used in this context, to "treat" means to ameliorate at least one symptom of the disorder to be treated or to provide a beneficial physiological effect. For compounds for the treatment of coronavirus, amelioration of a symptom could be inhibition of coronavirus replication or reduction of pneumonia related to coronavirus. Assessment of amelioration can be performed in many ways, including, but not limited to assessing active coronavirus infection, reduction in pneumonia, or reduction in other coronavirus-related symptoms.

Numerous embodiments are directed to the use of cyclic peptides as an antiviral (especially cyclic pentapeptides as an antiviral targeting coronavirus). In several embodiments, a subject to be treated is infected with a coronavirus or is at risk of coronavirus infection (e.g., prophylactic treatment). A number of coronavirus-related diseases can be treated, including (but not limited to) severe acute respiratory syndrome (SARS), middle east respiratory syndrome (MERS), coronavirus disease 2019 (COVID-19), multisystem inflammatory syndrome in children (MIS-C) and the common cold.

A therapeutically effective amount can be an amount sufficient to prevent reduce, ameliorate or eliminate the symptoms of diseases or pathological conditions susceptible to such treatment. In some embodiments, a therapeutically effective amount is an amount sufficient to inhibit viral replication in an infected individual.

Dosage, toxicity and therapeutic efficacy of the compounds can be determined, e.g., by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to non-infected cells.

Data obtained from cell culture assays or animal studies can be used in formulating a range of dosage for use in a subject. If the medicament is provided systemically, the dosage of such compounds lies preferably within a range of circulating concentrations that include the $ED_{50}$ with little or no toxicity. The dosage may vary within this range depending upon the dosage form employed and the route of administration utilized. For any compound used in a method of the various embodiments, the therapeutically effective dose can be estimated initially from cell culture assays. A dose may be formulated in animal models to achieve a circulating plasma concentration or within the local environment to be treated in a range that includes the $IC_{50}$ (i.e., the concentration of the test compound that achieves a half-maximal inhibition of coronavirus replication) as determined in cell culture. Such information can be used to more accurately determine useful doses in humans. Levels in plasma may be measured, for example, by liquid chromatography coupled to mass spectrometry. In some embodiments, a cytotoxic effect is achieved with an $IC_{50}$ less than 100 µM, 50 µM, 20 µM, 10 µM, or 5 µM.

An "effective amount" is an amount sufficient to effect beneficial or desired results. For example, a therapeutic amount is one that achieves the desired therapeutic effect. This amount can be the same or different from a prophylactically effective amount, which is an amount necessary to mitigate and/or prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments. For example, several divided doses may be administered daily, one dose, or cyclic administration of the compounds to achieve the desired therapeutic result. A single peptide compound of a particular formula may be administered, or combinations of various peptide compounds encompassing multiple formulas may be administered.

In a number of embodiments, peptide compounds are administered in combination with an appropriate standard of care, such as the standard of care established by an appropriate agency (e.g., the United States Federal Drug Administration (FDA)). In many embodiments, peptide compounds are administered in combination with other antiviral or immune stimulatory compounds, especially FDA-approved compounds. A number of FDA-approved compounds can be utilized, including (but not limited to) remdesivir, convalescent plasma, and tocilizumab.

A number of embodiments of formulations include those suitable for oral, pulmonary, or intravenous administration. Formulations may conveniently be presented in unit dosage form and may be prepared by any of the methods known in the art of pharmacy. Typically, these methods include the step of bringing into association a compound of at least one embodiment described herein, or a pharmaceutically salt, prodrug, or solvate thereof ("active ingredient") with the carrier which constitutes one or more accessory ingredients. Further, a pulmonary drug delivery (PDD) system may be utilized, for aerosol delivery via an inhaler, a nebulizer, dry powder, or any other appropriate system known in the art of pharmacy. Likewise, an intravenous drug delivery system may be utilized, for fluid delivery via a syringe, infusion (i.e., drips), or any other appropriate system known in the art of pharmacy.

Various agents can be incorporated that improve the solubility of the various compounds described herein. For example, various compounds can be formulated with one or more adjuvants and/or pharmaceutically acceptable carriers according to the selected route of administration. For oral applications, gelatin, flavoring agents, or coating material can be added. In general, for solutions or emulsions, including for use in pulmonary applications, carriers may include aqueous or alcoholic/aqueous solutions, emulsions or suspensions, including saline and buffered media. Parenteral vehicles can include sodium chloride and potassium chloride, among others. In addition, intravenous vehicles can include fluid and nutrient replenishers, electrolyte replenishers and the like.

For IV applications, numerous fluids can be utilized in accordance with various embodiments. In some embodiments, a crystalloid or colloid solution is utilized. Crystalloid solutions include (but are not limited to) saline (i.e., NaCl 0.9%), lactated Ringer's, and Ringer's acetate. Colloid solutions include (but are not limited to) blood, albumin, and plasma. Medications can be administered in a continuous infusion, a secondary infusion, or a bolus is utilized.

For oral applications, numerous coating agents can be used in accordance with various embodiments. In some embodiments, the coating agent is one which acts as a coating agent in conventional delayed release oral formulations, including polymers for enteric coating. Examples include hypromellose phthalate (hydroxy propyl methyl cellulose phthalate; HPMCP); hydroxypropylcellulose (HPC; such as KLUCEL®); ethylcellulose (such as ETHOCEL®); and methacrylic acid and methyl methacrylate (MAA/MMA; such as EUDRAGIT®).

Various embodiments of formulations also include at least one disintegrating agent, as well as diluent. In some embodiments, a disintegrating agent is a super disintegrant agent. One example of a diluent is a bulking agent such as a polyalcohol. In many embodiments, bulking agents and disintegrants are combined, such as, for example, PEARLITOL FLASH®, which is a ready to use mixture of mannitol and maize starch (mannitol/maize starch). In accordance with a number of embodiments, any polyalcohol bulking agent can be used when coupled with a disintegrant or a super disintegrant agent. Additional disintegrating agents include, but are not limited to, agar, calcium carbonate, maize starch, potato starch, tapioca starch, alginic acid, alginates, certain silicates, and sodium carbonate. Suitable super disintegrating agents include, but are not limited to crospovidone, croscarmellose sodium, AMBERLITE (Rohm and Haas, Philadelphia, Pa.), and sodium starch glycolate.

In certain embodiments, diluents are selected from the group consisting of mannitol powder, spray dried mannitol, microcrystalline cellulose, lactose, dicalcium phosphate, tricalcium phosphate, starch, pregelatinized starch, compressible sugars, silicified microcrystalline cellulose, and calcium carbonate.

Several embodiments of a formulation further utilize other components and excipients. For example, sweeteners, flavors, buffering agents, and flavor enhancers to make the dosage form more palatable. Sweeteners include, but are not limited to, fructose, sucrose, glucose, maltose, mannose, galactose, lactose, sucralose, saccharin, aspartame, acesulfame K, and neotame. Common flavoring agents and flavor enhancers that may be included in the formulation of the present invention include, but are not limited to, maltol, vanillin, ethyl vanillin, menthol, citric acid, fumaric acid, ethyl maltol and tartaric acid.

Multiple embodiments of a formulation also include a surfactant. In certain embodiments, surfactants are selected from the group consisting of Tween 80, sodium lauryl sulfate, and docusate sodium.

Many embodiments of a formulation further utilize a binder. In certain embodiments, binders are selected from the group consisting of povidone (PVP) K29/32, hydroxypropylcellulose (HPC), hydroxypropylmethylcellulose (HPMC), ethylcellulose (EC), corn starch, pregelatinized starch, gelatin, and sugar.

Various embodiments of a formulation also include a lubricant. In certain embodiments, lubricants are selected from the group consisting of magnesium stearate, stearic acid, sodium stearyl fumarate, calcium stearate, hydrogenated vegetable oil, mineral oil, polyethylene glycol, polyethylene glycol 4000-6000, talc, and glyceryl behenate.

Modes of administration, in accordance with multiple embodiments, include, but are not limited to, oral, pulmonary, transdermal, transmucosal (e.g., sublingual, nasal, vaginal or rectal), or parenteral (e.g., subcutaneous, intramuscular, intravenous, bolus or continuous infusion). The actual amount of drug needed will depend on factors such as the size, age and severity of disease in the afflicted individual. The actual amount of drug needed will also depend on the effective concentration ranges of the various active ingredients.

Embodiments of formulations disclosed herein suitable for oral administration may be presented as discrete units such as capsules, cachets or tablets each containing a predetermined amount of the active ingredient; as a powder or granules; as a solution or a suspension in an aqueous liquid or a nonaqueous liquid; or as an oil-in-water liquid emulsion or a water-in-oil liquid emulsion. Multiple embodiments also compartmentalize various components within a capsule, cachets, or tablets, or any other appropriate distribution technique.

Preservatives and other additives, like antimicrobial, antioxidant, chelating agents, and inert gases, can also be present. (See generally, Remington's Pharmaceutical Sciences, 16th Edition, Mack, (1980), the disclosure of which is incorporated herein by reference.)

Exemplary Embodiments

Biological data supports the use of the aforementioned cyclic peptides and their medicinal uses. Described within are details of various cyclic pentapeptides designed to inhibit the coronavirus $M^{pro}$. Inhibitory data is also provided.

A Cyclic Peptide Inhibitor of the SARS-CoV-2 Main Protease

This example presents the design and study of a first-in-class cyclic peptide inhibitor against the SARS-CoV-2 main protease ($M^{pro}$). The cyclic peptide inhibitor is designed to mimic the conformation of a substrate at a C-terminal autolytic cleavage site of $M^{pro}$. The cyclic peptide contains a [4-(2-aminoethyl)phenyl]-acetic acid (AEPA) linker that is designed to enforce a conformation that mimics a peptide substrate of $M^{pro}$. In vitro evaluation of the cyclic peptide inhibitor reveals that the inhibitor exhibits modest activity against $M^{pro}$ and does not appear to be cleaved by the enzyme. Conformational searching predicts that the cyclic peptide inhibitor is fairly rigid, adopting a favorable conformation for binding to the active site of $M^{pro}$. Computational docking to the SARS-CoV-2 $M^{pro}$ suggests that the cyclic peptide inhibitor can bind the active site of $M^{pro}$ in the predicted manner. Molecular dynamics simulations provide further insights into how the cyclic peptide inhibitor may bind the active site of $M^{pro}$.

Cyclic peptides are an important class of drugs. The binding affinities and specificities of cyclic peptides rival those of small molecule drugs and biomacromolecule drugs. Cyclic peptides often exhibit enhanced conformational stability and improved biological activity compared to linear analogues. This conformational rigidity increases resistance to degradation by endogenous proteases, leading to increased plasma stability. Peptide cyclization can also facilitate passage of the peptide through a cell membrane. Although cyclic peptides often do not meet common physicochemical guidelines for drug-like cellular uptake and bioavailability, such as Lipinski's Rules of 5, a variety of cyclic peptide drugs are active against intracellular targets.

Secondary structure and backbone rigidity often impart a greater propensity for cyclic peptides to cross the plasma membrane. The cyclic undecapeptide immunosuppressant drug cyclosporine A is an archetypal example for cell-permeable cyclic peptides. Despite its large size (MW=1202 Da), cyclosporine A is orally bioavailable and passively crosses the plasma membrane. Cyclosporine A achieves its remarkable permeability and bioavailability by adopting a rigid secondary structure comprising two β-strands connected by a β-turn to form an antiparallel β-sheet. The amide backbone of cyclosporine A is also highly methylated, and the remaining unmethylated NH groups are intramolecularly hydrogen-bonded.

Cyclic peptide inhibitors that target viral proteins, such as the SARS-CoV-2 main protease ($M^{pro}$), may offer promise as antiviral drugs with pharmacological properties similar to cyclosporine A. $M^{pro}$ is one of the best-characterized drug targets for coronaviruses. $M^{pro}$ cleaves the initially translated viral polyprotein into its component proteins within cells infected by SARS-CoV-2. Cleavage generally occurs immediately after a Gln residue, and the Gln residue is typically preceded by a hydrophobic residue, most often Leu. The residue that follows the Gln is often a small amino acid, such as Ser, Ala, or Asn. $M^{pro}$ autolytically cleaves itself from the polyprotein. Inhibiting $M^{pro}$ activity slows or halts viral replication, offering the promise of improved clinical outcomes for COVID-19 and other coronavirus diseases. Furthermore, there are no known human proteases with similar cleavage specificity to $M^{pro}$, suggesting that it should be possible to develop inhibitors that target $M^{pro}$ without off-target toxicity.

Peptide-based inhibitors previously developed to target the SARS-CoV $M^{pro}$ have effectively been repurposed and modified to target the SARS-CoV-2 $M^{pro}$-N3 from Jin et al., 13b from Zhang et al., and 11a and 11 b from Dai et al. (Z. Jin, et al., Nature. 2020; 582:289-293; W. Dai, et al., Science. 2020; 368:1331-1335; and L. Zhang, et al., Science. 2020; 368:409-412; the disclosures of which are each incorporated herein by reference). These inhibitors block SARS-CoV-2 replication in cell-based studies, making them promising antiviral drug candidates. While the $M^{pro}$ inhibitors N3, 13b, 11a, and 11b have shown promise against inhibiting SARS-CoV-2 replication, additional $M^{pro}$ inhibitors will most likely be needed for their improved properties or to be used in combination therapies.

Figure 7:
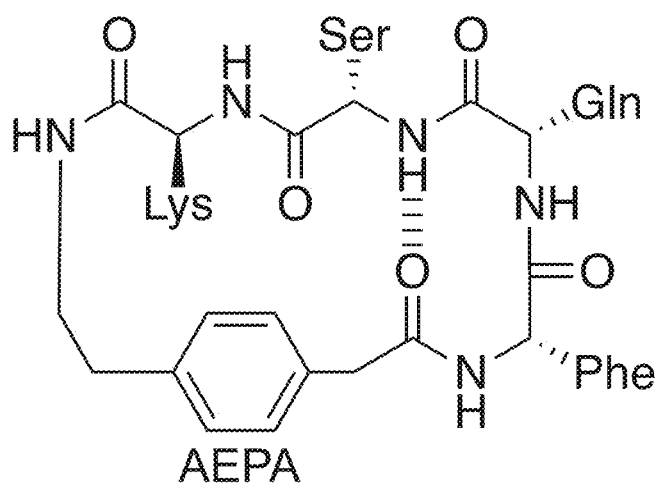
FIG. 7 provides a molecular structure diagram of cyclic peptide UCI-1 (SEQ ID NO: 58) in accordance with various embodiments.
Figure 8:
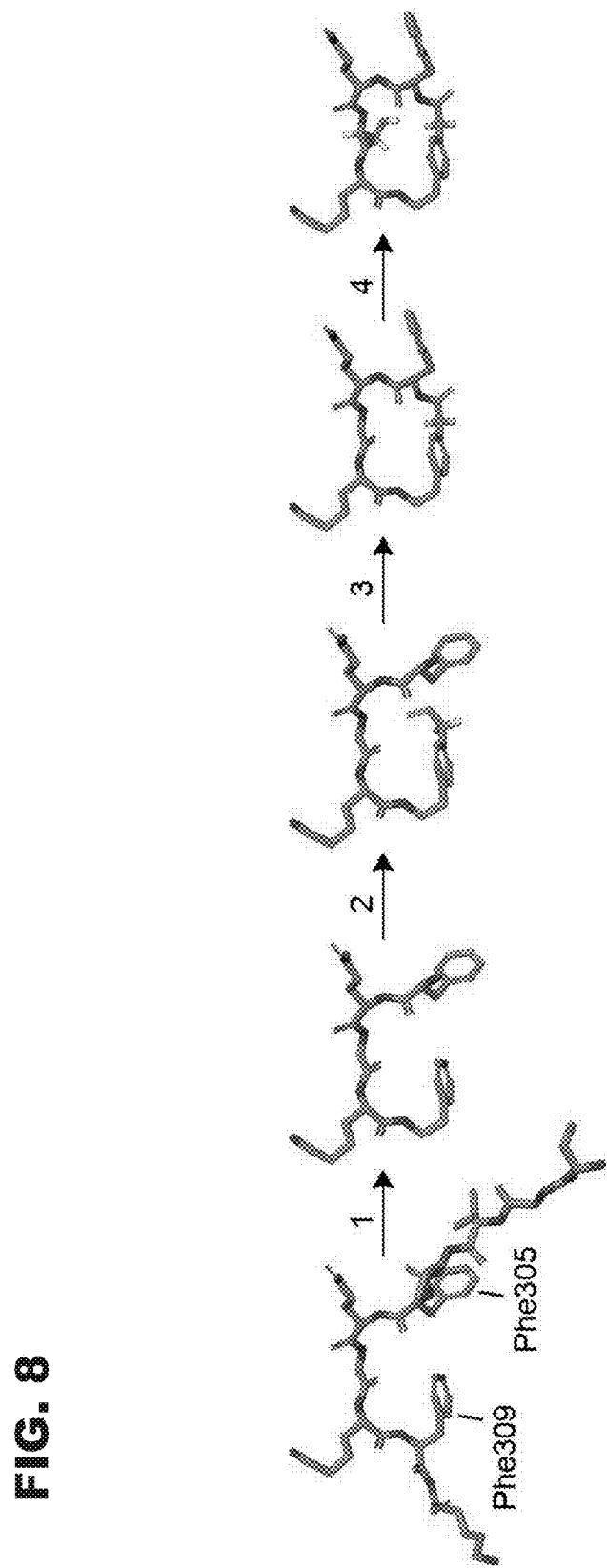
FIG. 8 provides molecular schematic diagram of a design process for creating the cyclic peptide inhibitor UCI-1 from the C-terminal autolytic substrate in the active site of $M^{pro}$ in accordance with various embodiments. (1) Delete residues 301-304 and 310 as well as the carbonyl of Phe309. (2) Build a $CH_2CO$ group on the para position of the phenyl group on Phe309. (3) Create a bond between the carbonyl carbon of the newly created $CH_2CO$ group on Phe309 and the amino group of Phe305 and minimize (clean) the structure. (4) Mutate Gly307 to serine.

Describe within this example is the design and in vitro evaluation of UCI-1 (University of California, Irvine Coronavirus Inhibitor-1), a first-in-class cyclic peptide that is designed to inhibit the SARS-CoV-2 $M^{pro}$, which is required for viral replication (FIG. 7). UCI-1 is a cyclic pentapeptide containing four amino acids from a $M^{pro}$ substrate constrained in a macrocycle linked together with a [4-(2-aminoethyl)phenyl]-acetic acid (AEPA) group to create a paracyclophane. This rigidified macrocycle is designed to mimic the conformation of a C-terminal autolytic cleavage site of a naturally occurring $M^{pro}$ substrate. Evaluation of UCI-1 in an in vitro $M^{pro}$ inhibition assay reveals that UCI-1 inhibits the SARS-CoV-2 $M^{pro}$ at mid-micromolar concentrations. LC/MS analysis indicates that UCI-1 resists cleavage by $M^{pro}$ despite containing a scissile amide bond. Furthermore, UCI-1 is found to be non-toxic toward human embryonic kidney cells at concentrations that inhibit $M^{pro}$.

Results

Design of UCI-1.

The cyclic peptide inhibitor UCI-1 was designed based on the crystal structure of an inactive SARS-CoV $M^{pro}$ (C145A) variant with a 10 amino-acid C-terminal extension corresponding to the C-terminal prosequence of $M^{pro}$ (PDB 5660) ("$M^{pro}_{316}$") (T. Muramatsu, et al., Proc Natl Acad Sci USA. 2016; 113:12997-13002, the disclosure of which is incorporated herein by reference). The SARS-CoV $M^{pro}$ amino acid sequence is 96% identical to the SARS-CoV-2 $M^{pro}$ amino sequence, and the three-dimensional structure of the SARS-CoV-2 $M^{pro}$ is highly similar to the structure of the SARS-CoV $M^{pro}$. In the $M^{pro}_{316}$ crystal structure, C-terminal residues 301-310 (SGVTFQGKFK; SEQ. ID No. 56) extend into and complex with the active site of another $M^{pro}_{316}$ molecule in an adjacent asymmetric unit (FIG. 3). This complex reveals how the P2-P1-P1'-P2'-P3' positions (residues 305-309, FQGKF; SEQ ID No. 1) of the C-terminal autolytic cleavage site fit into the active site of $M^{pro}_{316}$.

UCI-1 was designed to mimic the conformation that the P2-P1-P1'-P2'-P3' residues adopt in the active site of $M^{pro}_{316}$. In the active site of $M^{pro}_{316}$, these residues adopt a "kinked" conformation in which the phenyl group of Phe309 at the P3' position points toward the backbone of Phe305 at the P2 position (FIG. 3). To mimic this conformation, the phenyl group of Phe309 could be linked to the backbone of Phe305 to create a macrocycle. To realize this design, the molecular visualization software PyMOL (version 2.2.2, Schrödinger) was used to build a model of the envisioned cyclic peptide by modifying Phe305 and Phe309 in the active site of $M^{pro}$ 316 (FIG. 3). In PyMOL, residues 301-304 were deleted to expose the amino group on Phe305; residue 310 and the carbonyl of Phe309 were also deleted. The para position of Phe309 was then connected to the amino group of Phe305 with a $CH_2CO$ group to create a macrocycle. The newly created amino acid derived from Phe309 thus constitutes the amino acid AEPA.

It was recognized that upon linking Phe309 and Phe305 as described above, Phe305 and Gln306 were poised to form a β-turn in which the carbonyl group of AEPA hydrogen bonds with the amino group of Gly307. It was envisioned that β-turn formation in the cyclic peptide inhibitor would promote rigidity of the cyclic scaffold. To introduce additional conformational rigidity to the macrocycle, Gly307 was mutated to serine, which is the most common residue at the P1' position among the 11 known SARS-CoV-2 $M^{pro}$ cleavage sites. The resulting cyclic peptide inhibitor UCI-1 was then further studied as described below.

Figure 9:
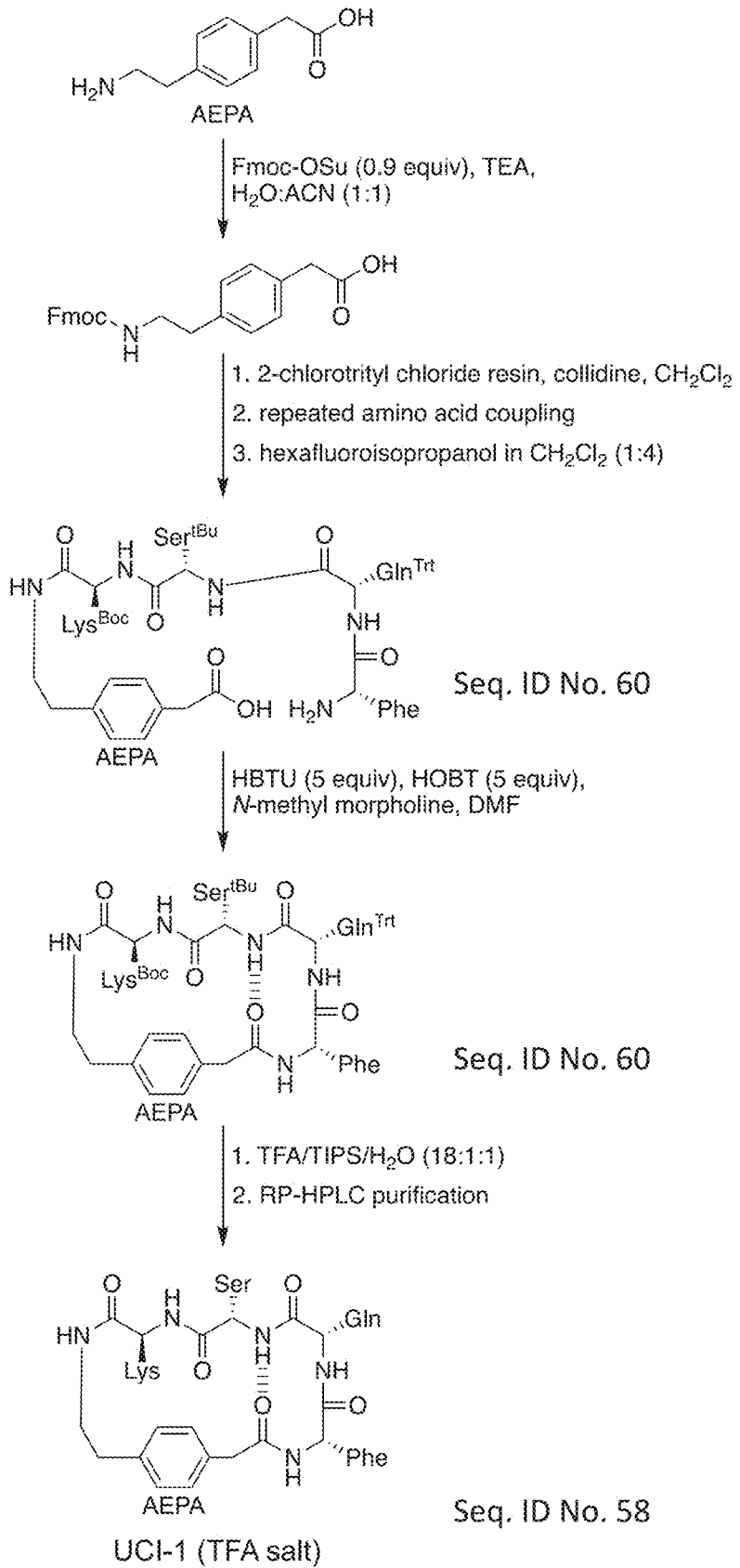
FIG. 9 provides a schematic of the synthesis of UCI-1 (SEQ ID NO: 58) in accordance with various embodiments. Intermediate peptide corresponds with SEQ ID NO: 60.

Synthesis of UCI-1. UCI-1 was synthesized by Fmoc-based solid-phase peptide synthesis of the protected linear peptide $H_2N$-FQSK-AEPA-COOH (SEQ. ID No. 58) on 2-chlorotrityl chloride resin, followed by cleavage of the linear protected peptide from the resin and subsequent solution-phase macrocyclization and global deprotection (FIG. 9). UCI-1 was purified using reverse-phase HPLC. The synthesis and purification proceeded smoothly on a 0.1 mmol scale and yielded 22 mg of purified UCI-1 as the TFA salt. Detailed procedures for synthesis of UCI-1 are given in the Materials and Methods section.

Enzyme Inhibition Assay.

Figure 10:
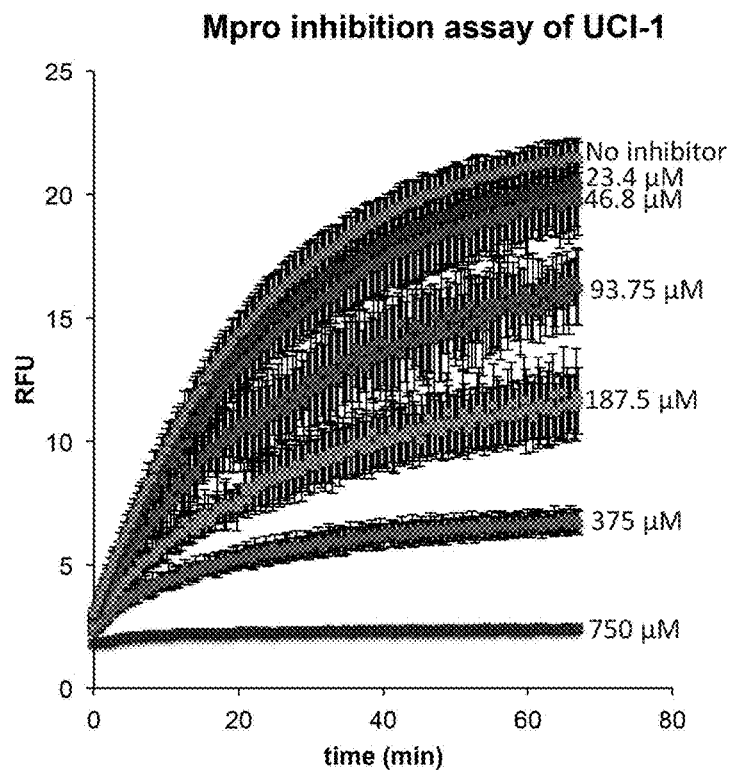
FIG. 10 provides a data graph of continuous kinetic inhibition assay of UCI-1 against $M^{pro}$ in accordance with various embodiments.
Figure 11:
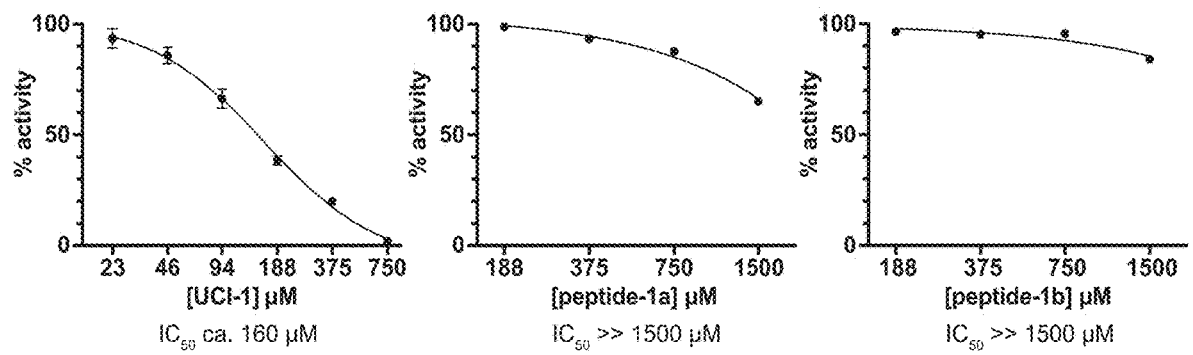
FIG. 11 provides data graphs depicting enzyme inhibition assay of UCI-1 and control peptides peptide-1a and peptide-1b, generated in accordance with various embodiments. The activity of $M^{pro}$ was measured in the presence of increasing concentrations of UCI-1, peptide-1a, or peptide-1b. A dose-response curve was determined by non-linear regression and used to estimate the $IC_{50}$. All data are shown as the mean of three technical replicates, with error bars representing the standard deviation.

To evaluate whether UCI-1 inhibits the SARS-CoV-2 $M^{pro}$, a fluorescence-based $M^{pro}$ inhibition assay was used having native $M^{pro}$ (Life Sensors) and the fluorogenic $M^{pro}$ substrate K(Dabcyl)-TSAVLQSGFRKM-E(EDANS)-$NH_2$ (SEQ. ID No. 57). For the inhibition assay, $M^{pro}$ was pre-incubated with varying concentrations of UCI-1 (23.4-750 µM) in assay buffer for 30 min. After pre-incubation, the fluorogenic $M^{pro}$ substrate was added and $M^{pro}$ activity was monitored in a continuous kinetic assay with 360 nm excitation and 460 nm emission. In each well, the concentration of $M^{pro}$ was 0.1 µM and the concentration of the fluorogenic substrate was 50 µM. FIG. 10 shows the data from the continuous kinetic assay. Initial rates for $M^{pro}$ activity in the presence or absence of UCI-1 were obtained by fitting a straight line to the linear portions of the curves from the continuous kinetic assay. The % activity was calculated by comparing the initial rate at each concentration to the initial rate in the absence of inhibitor. Non-linear regression was then used to fit the data and estimate an $IC_{50}$ of ca. 160 µM for UCI-1 (FIG. 11 left panel).

Figure 12:
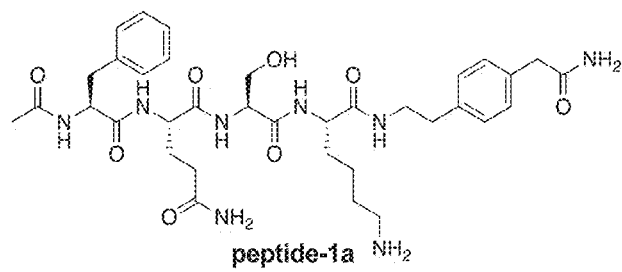
FIG. 12 provides molecular structure diagrams of peptide-1a (SEQ ID NO:58) and peptide-1b (SEQ ID NO:58) in accordance with various embodiments.
Figure 12:
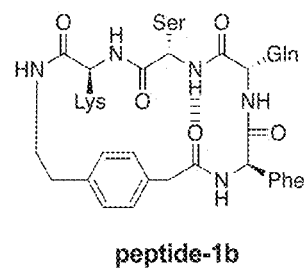

To better understand the significance of inhibition of $M^{pro}$ by UCI-1, two control peptides we synthesized and tested. The peptides were derived from UCI-1—the acyclic analog of UCI-1 "peptide-1a" and the diastereomer "peptide-1b" (FIG. 12)—that were predicted to not inhibit $M^{pro}$. Peptide-1a exhibits little or no inhibition at concentrations at or below 750 µM (FIG. 11 middle panel). This finding indicates that the cyclic structure of UCI-1 is important for its activity. There is a slight reduction in rate of cleavage of the fluorogenic substrate upon addition of 1500 µM peptide-1a. This reduction in rate may reflect either slight inhibition of $M^{pro}$ or that the acyclic peptide acts as a competitive substrate at high concentrations. Peptide-1b exhibits little or no inhibition at concentrations at or below 1500 µM (FIG. 11 right panel). The inactivity of peptide-1b suggests that the shape and stereochemistry of UCI-1 are critical for fitting into and blocking the active site of $M^{pro}$, and that inhibition by UCI-1 does not simply result from its hydrophobicity and cyclic structure.

Conformational Analysis, Docking, and Molecular Dynamics Simulations of UCI-1.

Figure 13A:
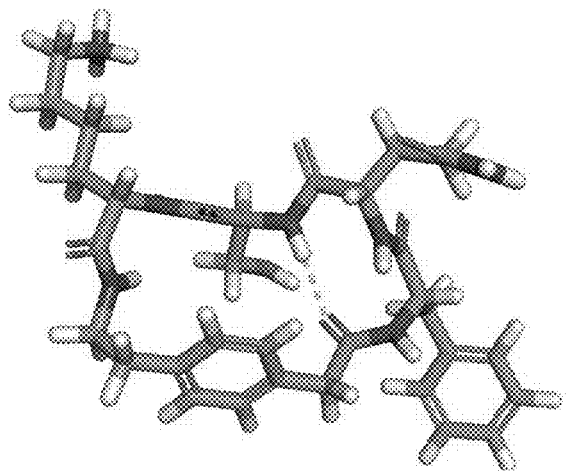
FIG. 13A provides a molecular structure diagram of the lowest energy conformer of UCI-1 in accordance with various embodiments.

To better understand the three-dimensional structure of UCI-1 and how it could interact with the active site of the SARS-CoV-2 $M^{pro}$, conformational analysis and docking studies were performed. Conformational searching of UCI-1 (MacroModel with the MMFFs force field and GB/SA water) revealed that UCI-1 adopts a global minimum energy conformation that resembles the kinked conformation that residues 305-309 adopt in the active site of $M^{pro}_{316}$ (FIGS. 2 and 13A). In the global minimum energy conformation, the AEPA residue acts as a rigid spacer, with Phe, Gln, Ser, and Lys forming a bridge. As envisioned, the Phe and Gln residues adopt a β-turn conformation, with Phe at the i+1 position and Gln at the i+2 position. The Phe side chain is well situated to fit into the S2 pocket, and the Gln side chain is well situated to fit into the S1 pocket. The Ser, Lys, and AEPA residues, in turn, are poised to occupy the S1', S2', and S3' pockets.

Figure 13B:
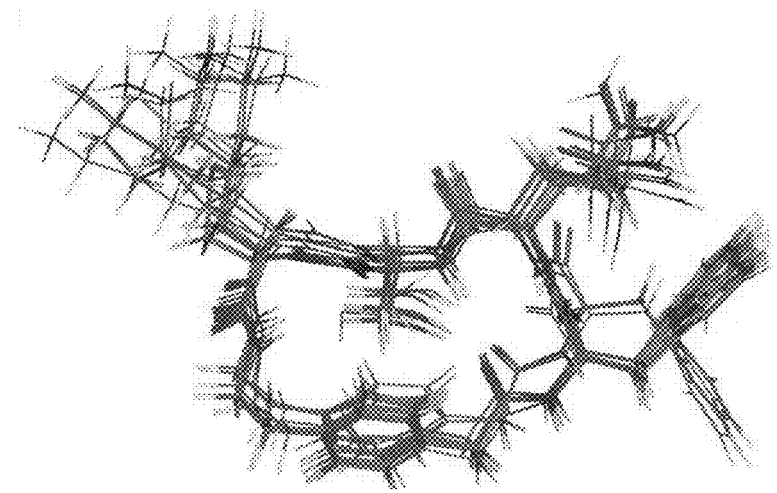
FIG. 13B provides molecular structure diagrams of the 20 lowest energy conformers from conformational searching superimposed on one another in accordance with various embodiments. The difference in energy between the lowest and highest energy conformers among these 20 is 7.0 kJ/mol.
Figure 13C:
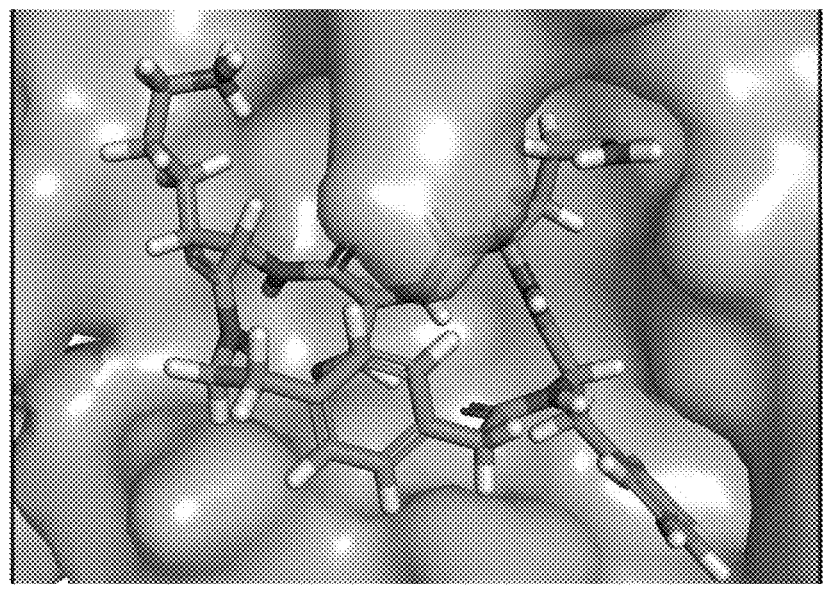
FIG. 13C provides a molecular structure diagram of UCI-1 in complex with the SARS-CoV-2 $M^{pro}$ active site, generated in accordance with various embodiments. The SARS-CoV-2 $M^{pro}$ crystal structure with PDB accession number 6YB7 was used in the docking study.

The cyclic peptide appears to be particularly rigid. In the conformational search, the peptide backbones of most of the conformers adopt the conformation described above, differing only in side chain geometry and the type of β-turn formed by Phe305 and Gln306 (FIG. 13B). To evaluate how UCI-1 might fit in the active site of $M^{pro}$, UCI-1 was docked with the X-ray crystallographic structure of the SARS-CoV-2 $M^{pro}$ PDB 6YB7 using Autodock Vina (O. Trott and A. J. Olson, J Comput Chem. 2010; 31:455-61, the disclosure of which is incorporated herein by reference). This initial docking study revealed that UCI-1 fits into the active site of the SARS-CoV-2 $M^{pro}$ in the envisioned manner (FIG. 13C).

To further evaluate how UCI-1 may achieve inhibition of $M^{pro}$, a complementary docking experiment was performed on UCI-1, and then performed a molecular dynamics simulation on the docked structure. In this study, UCI-1 was first docked with an equilibrated version of the X-ray crystallographic structure of the SARS-CoV-2 $M^{pro}$ dimer PDB 6Y2E, which has previously been simulated in explicit water (T. J. Cross, et al., Biochemistry. 2020; 59:3741-3756, the disclosure of which is incorporated herein by reference). Next, a low-energy configuration of UCI-1 bound to an equilibrated crystal structure of the $M^{pro}$ dimer PDB 6Y2E was chosen that best matched the docked structure observed in the initial docking experiment with PDB 6YB7. Finally, 10 ns of molecular dynamics simulation of the docked structure was performed using the CHARMM36 force field and TIP3P water at 310 Kelvin. This procedure was then repeated for peptide-1a and peptide-1b to gain insight into why these control peptides do not substantially inhibit $M^{pro}$.

Figure 14:
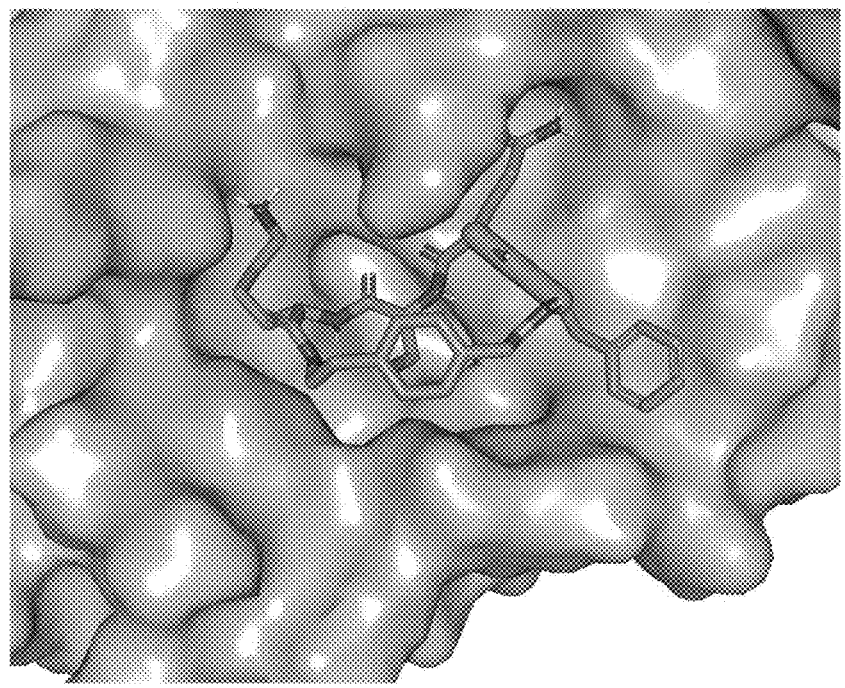
FIG. 14 provides a molecular structure diagram of low-energy configuration of UCI-1 docked to an equilibrated crystal structure of the $M^{pro}$ dimer PDB 6Y2E in accordance with various embodiments. This docked structure was used as the initial conditions in the 10 ns trajectory in the molecular dynamics simulation.
Figure 15:
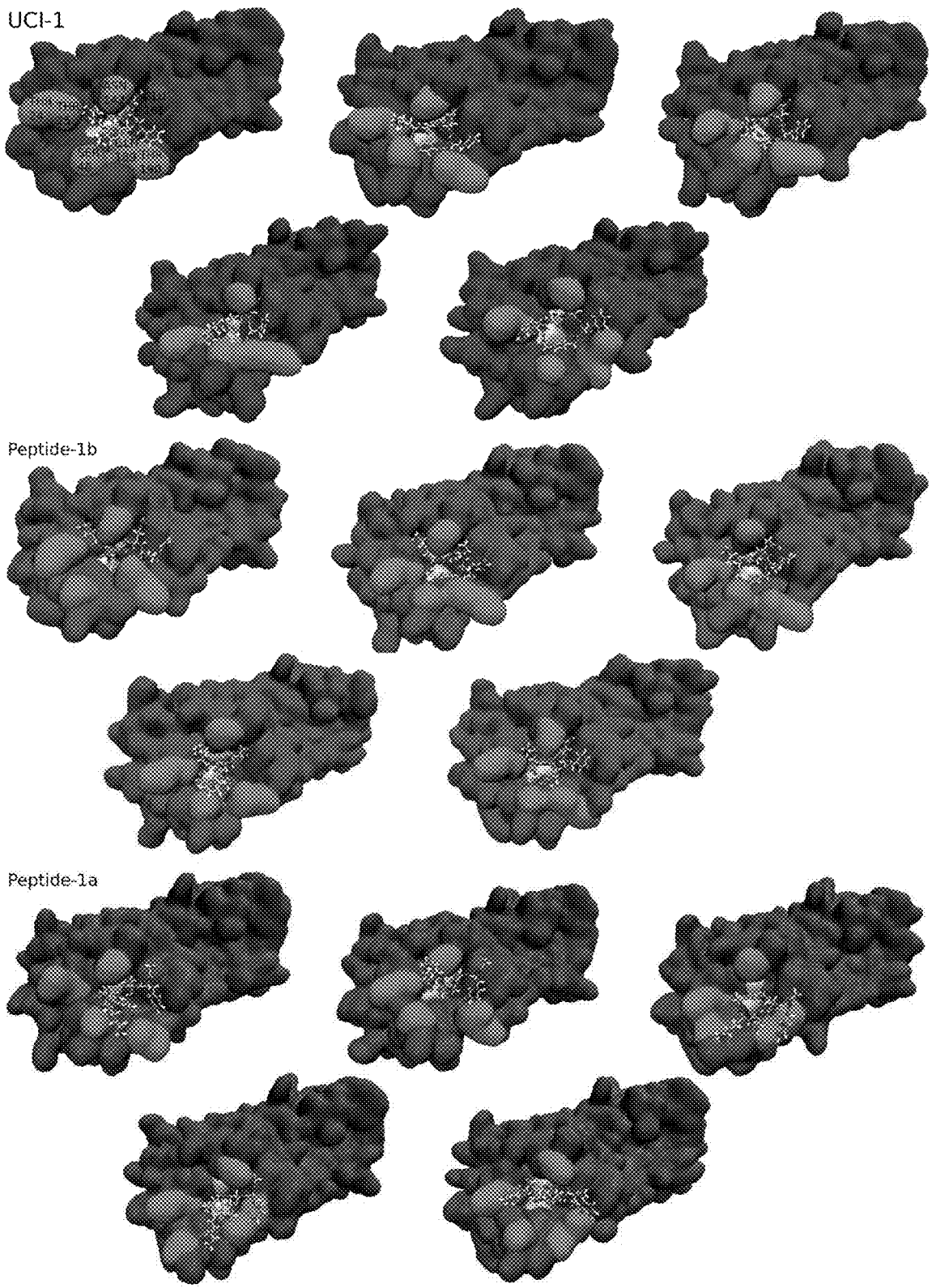
FIG. 15 provides select frames from a 10 ns molecular dynamics simulation of UCI-1, peptide-1b, and peptide-1a docked to $M^{pro}$ PDB 6Y2E, generated in accordance with various embodiments.

In the UCI-1 docking experiment, the side chains of UCI-1 occupy the active site $M^{pro}$ in the envisioned manner, where Phe occupies the S2 pocket, Gln occupies the S1 pocket, Ser occupies the S1' pocket, Lys occupies the S2' pocket, and the AEPA group occupies the S3' pocket (FIG. 14). Over the course of the simulation, UCI-1 stays bound to the active site and the amino acids maintain their positions in the pockets of the active site—only the Lys side chain appears to leave its respective pocket over the 10 ns simulation (Figure S3). In contrast, the control peptides explore more of the active site and their side chains do not remain in their respective pockets as frequently. Notably, the d-Phe side chain of peptide-1b does not stay in the S2 pocket, and at times travels towards the S3' pocket, causing the peptide to lift away from the active site. The linear control, peptide-1a, does not appear to bind well in any of the pockets.

Stability of UCI-1 Toward $M^{pro}$.

Figure 16:
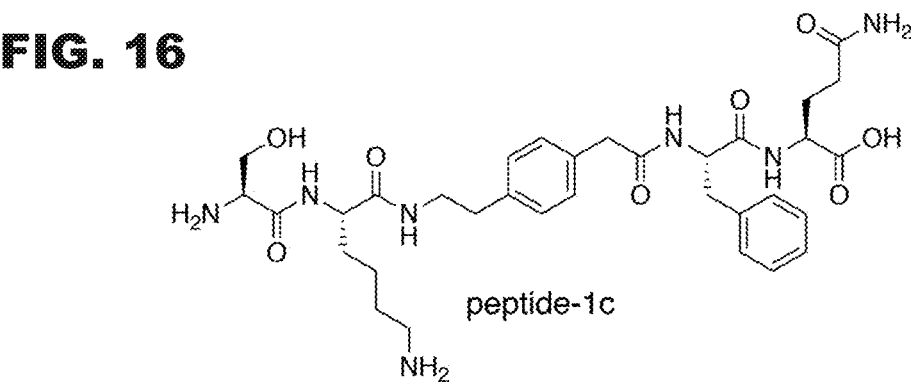
FIG. 16 a molecular structure diagram of peptide-1c in accordance with various embodiments.

The amide bond between residues at positions P1 and P1' of UCI-1 has the potential to be cleaved by $M^{pro}$, because residues at these positions correspond to the cleavage site of $M^{pro}$ substrates. To determine whether $M^{pro}$ cleaves UCI-1, LC/MS was used to analyze UCI-1 in the well solution from the 96-well plate of the enzyme inhibition assay after 4 hours. To aid in LC/MS identification of the cleavage product of UCI-1, peptide-1c was synthesized (FIG. 16), which would correspond to the authentic UCI-1 $M^{pro}$ cleavage product. The well solution was then spiked with peptide-1c to identify and determine the limits of detection of the putative cleavage product.

Figure 17A:
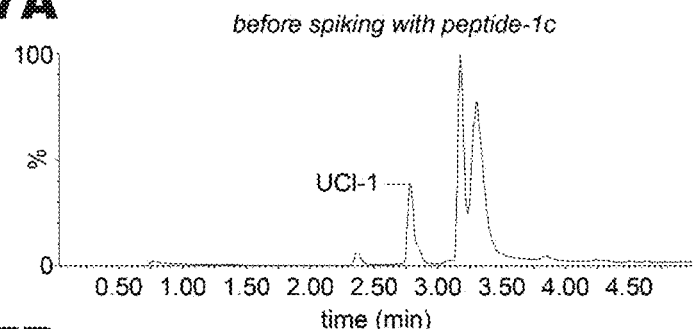
FIGS. 17A to 17D provide LC/MS data assessing cleavage of UCI-1 by $M^{pro}$, generated in accordance with various embodiments.
Figure 17B:
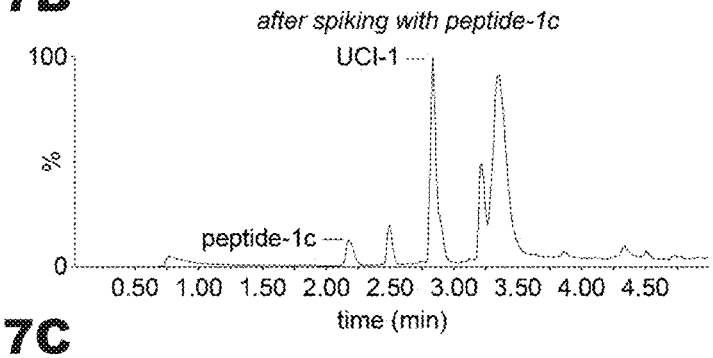
Figure 17C:
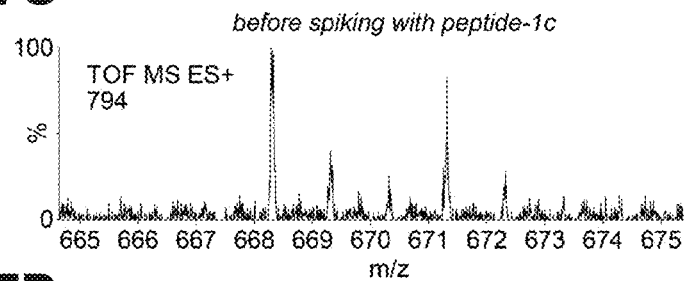
Figure 17D:
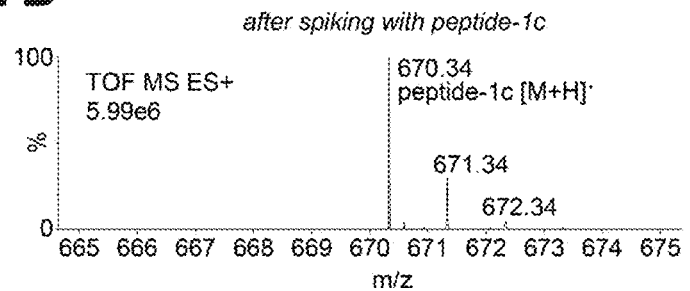

UCI-1 is not appreciably cleaved by $M^{pro}$ (FIGS. 17A-D). LC/MS analysis of 5 µL of the 187.5 µM UCI-1 enzyme inhibition assay well solution spiked with 20 µM peptide-1c shows a peak at 2.2 minutes that corresponds to peptide-1c (FIG. 17B). The peak at 2.2 minutes is absent in the LC/MS trace acquired before spiking the well solution with peptide-1c (FIG. 17A), indicating that there is little to no cleavage of UCI-1 by $M^{pro}$. The ion current at 2.2 minutes in the LC/MS trace acquired before spiking with peptide-1c shows no significant evidence of the UCI-1 cleavage product (FIG. 17C), whereas the ion current at 2.2 minutes in the LC/MS trace acquired after spiking with peptide-1b shows the mass of peptide-1c (FIG. 17D), providing additional evidence that UCI-1 resists cleavage by $M^{pro}$. These findings confirm that UCI-1 acts as an inhibitor and not a competitive substrate. The resistance of UCI-1 to cleavage by $M^{pro}$ is consistent with the observations by others that cyclic peptides often resist proteolytic cleavage.

Cytotoxicity of UCI-1.

Figure 18:
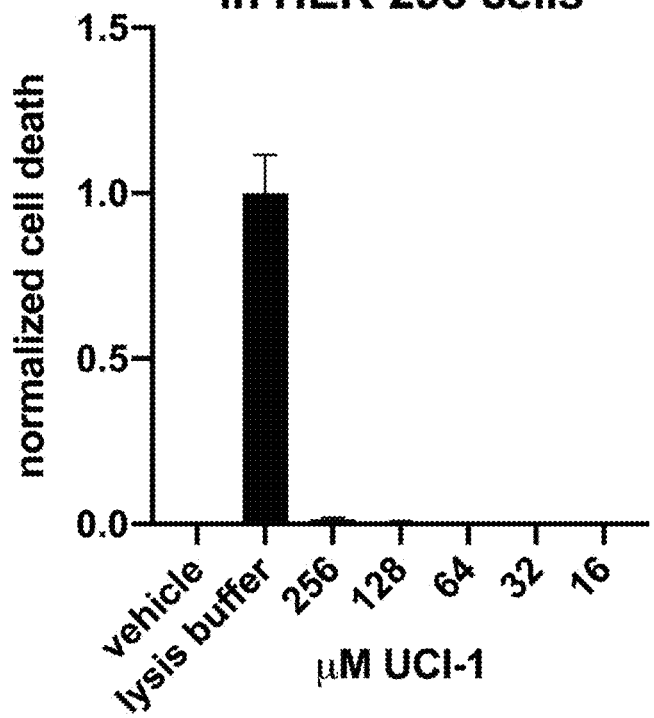
FIG. 18 provides a bar graph depicting LDH release assay of UCI-1 in HEK-293 cells, generated in accordance with various embodiments. All data are shown as mean±s.d., n=5 replicates. Deionized water (vehicle) was used as a negative control.

To evaluate whether UCI-1 is cytotoxic, human embryonic kidney (HEK-293) cells were exposed to varying concentrations of UCI-1 (0-256 µM) for 72 hours, and then assessed cell death using a lactate dehydrogenase (LDH) release assay. At the highest concentration evaluated, UCI-1 elicits little or no LDH release from HEK-293 cells, indicating that UCI-1 is not cytotoxic at concentrations up to 256 µM (FIG. 18).

Discussion

UCI-1 is noteworthy, because it represents a direct creation of a cyclic peptide inhibitor of $M^{pro}$ from the crystal structure of a linear peptide substrate. UCI-1 is created from the linear peptide substrate by the addition of only a single methylene group to the para position of Phe309 that is then linked to the backbone carbonyl of Phe305 to create a rigid peptide macrocycle linked together by AEPA. In synthesizing UCI-1, the cyclization proceeds smoothly, without formation of detectable oligomers, uncyclized linear peptide, or side products.

Figure 19:
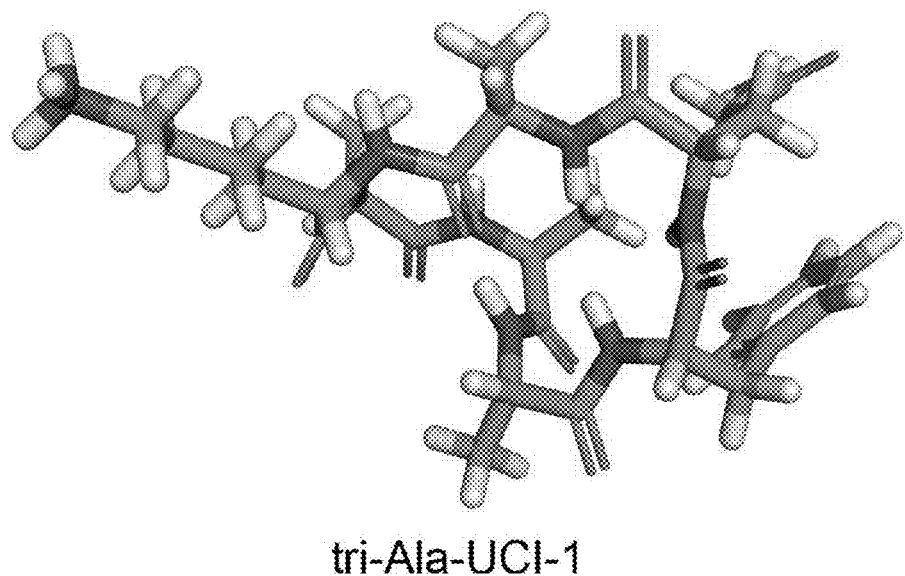
FIG. 19 provides a molecular structure diagram of tri-Ala-UCI-1 in accordance with various embodiments.

The apparent rigidity of UCI-1 demonstrates an emergent property of the AEPA linker, whereby a short strand of amino acids can span across the AEPA linker to create a macrocycle that adopts a β-turn structure and a doughnut-like shape. To further evaluate the utility of the AEPA linker, a homologue of UCI-1 was designed in which the rigid AEPA linker was replaced with a flexible tri-alanine linker (tri-Ala-UCI-1) and performed conformational searching of this homologue (MacroModel with the MMFFs force field and GB/SA water). Like UCI-1, tri-Ala-UCI-1 is a 21-membered macrocycle. Conformational searching of tri-Ala-UCI-1 reveals that the global minimum energy conformation of tri-Ala-UCI-1 adopts a compact closed structure, rather than an open structure (FIG. 19). While UCI-1 contains an open ring with a stabilizing β-turn structure and a "kinked" conformation that resembles the conformation of the linear peptide $M^{pro}$ substrate, tri-Ala-UCI-1 lacks these features. Because the AEPA amino acid replaces a tripeptide and enforces an open structure, it is a useful template for inducing a well-defined conformation in the spanning tetrapeptide.

Figure 20:
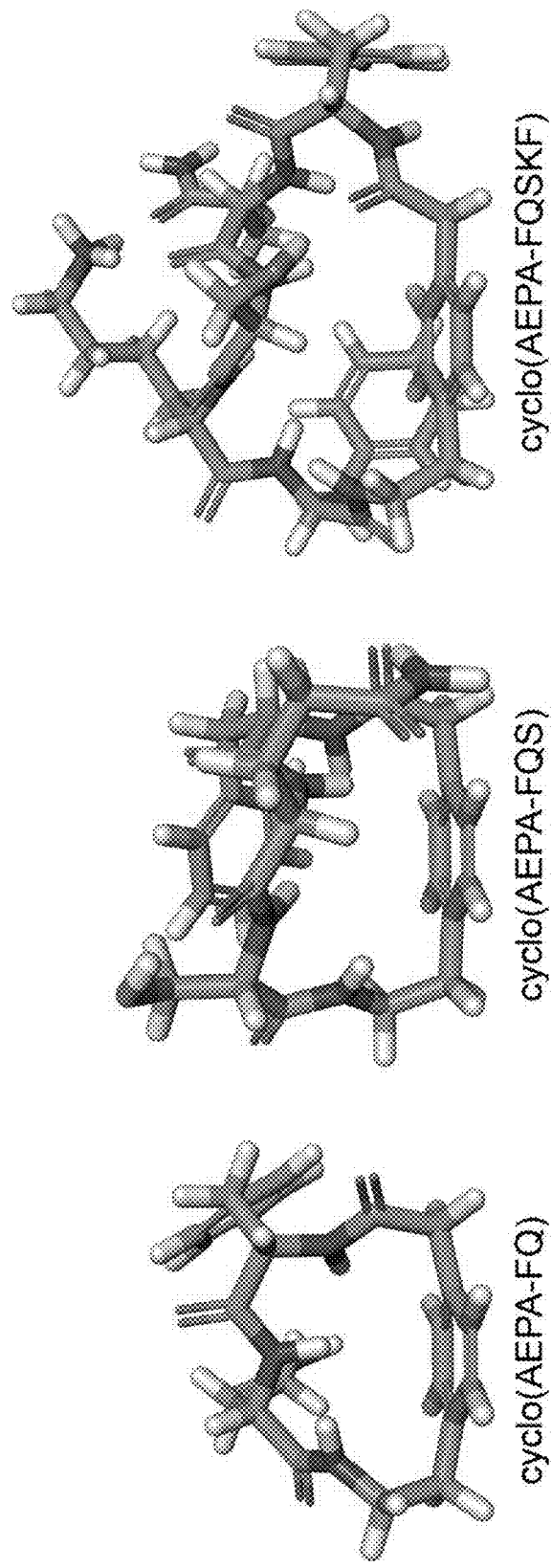
FIG. 20 provides molecular structure diagrams of global minimum energy conformations of homologous AEPA macrocycles derived from UCI-1 that contain two, three (SEQ ID NO: 61) and five (SEQ ID NO: 59) amino acids spanned across the AEPA linker.

UCI-1 is a paracyclophane containing four α-amino acids, in addition to AEPA. Conformationally constrained paracyclophane macrocycles containing AEPA and two, three, or five α-amino acids can also be envisioned. Molecular modeling of homologous AEPA macrocycles derived from UCI-1 with two, three, and five amino acids demonstrates that all the macrocycles adopt doughnut-like open structures in which the amino acids are extended above the AEPA linker (FIG. 20). In additional modeling studies, it was found that AEPA macrocycles that contain amino acids other than glycine adopt this open doughnut-like structure. Macrocycles containing only two α-amino acids are strained to the point of bending the AEPA unit out of planarity—a common property of smaller paracyclophanes (FIG. 20). Nevertheless, cyclo(AEPA-FQ) was able to be synthesized and the cyclization proceeded smoothly, without the formation of detectable oligomers, uncyclized linear peptide, or side products.

Conclusion

In spite of the rapid development of vaccines to combat COVID-19, antiviral drugs are still needed. Antiviral drugs that slow or halt viral replication can lead to a shortened time to recovery from COVID-19, offering the promise of improved mortality rates and alleviating the tremendous strain experienced by hospitals during the COVID-19 pandemic. Antiviral drugs could also be used as first line of defense in a future coronavirus outbreak or pandemic, or even as a prevention.

The design of the UCI-1 demonstrates that cyclic peptides that mimic the conformation of linear peptide substrates of $M^{pro}$ can be inhibitors against $M^{pro}$. Almost all of the $M^{pro}$ inhibitors that have been reported thus far are linear peptides that contain a "warhead" that forms a covalent bond with the active cysteine of $M^{pro}$. While the activity of UCI-1 is modest compared to other known $M^{pro}$ inhibitors, UCI-1 lays the groundwork for developing additional cyclic peptide inhibitor analogues with improved activity against $M^{pro}$. AEPA has been found to be useful in the design of other conformationally constrained cyclic peptides with potential pharmacological applications.

Materials and Methods

Synthesis of 2-(4-(2-((((9H-fluoren-9-yl)methoxy)carbonyl)amino)ethyl)phenyl)acetic Acid (Fmoc-AEPA)

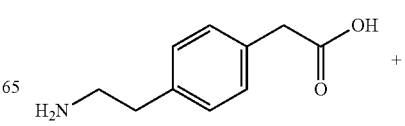

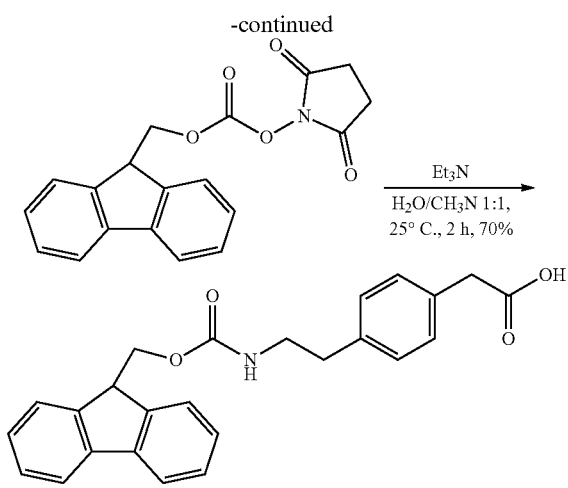

A 50 mL round-bottom flask equipped with a magnetic stirring bar was charged with 100 mg (0.55 mmol, 1 equiv) of 2-(4-(2-aminoethyl)phenyl)acetic acid dissolved in 10 mL H$_2$O. 0.156 mL (1.10 mmol, 2 equiv) of Et$_3$N was added. 160 mg of Fmoc-OSu (0.50 mmol, 0.9 equiv) was dissolved in 10 mL CH$_3$CN and added to the reaction mixture. The reaction was run for 2 hours at room temperature. While it was running, the reaction was monitored by TLC (3:1 EtOAc/hexanes+10% MeOH, R$_f$=0.44) to determine the consumption of starting material (R$_f$=0.77) and an appearance of fulvene (R$_f$=0.81). 10 mL of EtOAc was then added to the reaction mixture and the organic layer was removed. The aqueous layer was acidified with 30 mL 1 M HCl, and then 10 mL of EtOAc was added. The organic layer was washed with water and brine, dried over MgSO$_4$, and solvent was evaporated in vacuo to afford 0.140 g (70%) of Fmoc-AEPA-OH as a white powder. The Fmoc-AEPA-OH was used in solid-phase peptide synthesis without further purification. The product contains a minor contaminant (<10%) of Fmoc-AEPA-AEPA-OH, as detected by $^1$H NMR spectroscopy. HRMS (ESI-TOF) m/z: [M+Na]$^+$ calcd for C$_{25}$H$_{23}$NO$_4$Na 424.1525. found 424.1507.

Syntheses of UCI-1 and Peptide-1b.

2-Chlorotrityl chloride resin (300 mg, 1.6 mmol/g) was added to a Bio-Rad Poly-Prep chromatography column (10 mL). The resin was suspended in dry CH$_2$Cl$_2$ (10 mL) and allowed to swell for 30 min. The solution was drained from the resin and a solution of Fmoc-AEPA-OH (0.50 equiv, 64 mg, 0.16 mmol) in 6% (v/v) 2,4,6-collidine in dry CH$_2$Cl$_2$ (8 mL) was added immediately and the suspension was gently agitated for 12 h. The solution was then drained and a mixture of CH$_2$Cl$_2$/MeOH/N,N-diisopropylethylamine (DIPEA) (17:2:1, 10 mL) was added immediately. The mixture was gently agitated for 1 h to cap the unreacted 2-chlorotrityl chloride resin sites. The resin was then washed with dry CH$_2$Cl$_2$ (2×) and dried by passing nitrogen through the vessel. This procedure yielded 0.51 mmol/g of loaded resin.

The Fmoc-AEPA-2-chlorotrityl resin was transferred to a peptide synthesis coupling vessel and subjected to cycles of peptide coupling with Fmoc-protected amino acid building blocks. The linear peptide was synthesized from the C-terminus to the N-terminus. Each coupling cycle consisted of i. Fmoc-deprotection with 20% (v/v) piperidine in DMF for 5 min (2×), ii. washing with DMF (3×), iii. coupling of the amino acid (5 equiv) in the presence of HCTU (4.5 equiv) and 20% (v/v) N-methylmorpholine (2,4,6-collidine) in DMF for 10-20 min. iv. washing with DMF (3×). After coupling of the last amino acid, the terminal Fmoc group was removed with 20% (v/v) piperidine in DMF. The resin was transferred from the coupling vessel to a Bio-Rad Poly-Prep chromatography column.

The linear peptide was cleaved from the resin by agitating the resin for 1 h with a solution of 1,1,1,3,3,3-hexafluoroisopropanol (HFIP) in CH$_2$Cl$_2$ (1:4, 7 mL). The suspension was filtered and the filtrate was collected in a 250-mL round-bottomed flask. The resin was washed with additional HFIP in CH$_2$Cl$_2$ (1:4, 7 mL) and then with CH$_2$Cl$_2$ (2×10 mL). The combined filtrates were concentrated by rotary evaporation to give a white solid. The white solid was further dried by vacuum pump to afford the crude protected linear peptide, which was cyclized without further purification.

The crude protected linear peptide was dissolved in dry DMF (150 mL). HOBt (5 equiv) and HBTU (5 equiv) were added to the solution. NMM (12 equiv) was added to the solution and the mixture was stirred under nitrogen for 24 h. The mixture was then concentrated under reduced pressure to afford the crude protected cyclic peptide.

The protected cyclic peptide was dissolved in TFA/triisopropylsilane (TIPS)/H$_2$O (18:1:1, 20 mL) in a 250-mL round-bottomed flask equipped with a nitrogen-inlet adaptor. The solution was stirred for 1.5 h. The reaction mixture was then concentrated by rotary evaporation under reduced pressure to afford the crude cyclic peptide as a thin yellow film on the side of the round-bottomed flask. The crude cyclic peptide was immediately subjected to purification by reverse-phase HPLC (RP-HPLC).

The peptide was dissolved in H$_2$O and acetonitrile (7:3, 10 mL), and the solution was filtered through a 0.2 μm syringe filter and purified by RP-HPLC (gradient elution with 10-30% CH$_3$CN over 50 min). Pure fractions were concentrated by rotary evaporation and lyophilized. The synthesis of UCI-1 yielded 22 mg (18.7% based on resin loading) of the peptide as the TFA salt. The synthesis of peptide-1b yielded 16 mg (13.6% based on resin loading) of the peptide as the TFA salt.

Synthesis of Peptide-1a.

Rink amide AM resin (300 mg, 0.68 mmol/g) was added to a peptide synthesis coupling vessel. The resin was suspended in dry DMF (10 mL) and allowed to swell for 30 min. The solution was drained from the resin and the Fmoc group was removed with 20% (v/v) piperidine in DMF for 20 min. The solution was drained and washed with DMF (5×). Fmoc-AEPA-OH (0.50 equiv, 40.8 mg, 0.102 mmol), HATU (0.5 equiv), and HOAt (0.5 equiv) in 20% (v/v) 2,4,6-collidine in dry DMF (8 mL) was then added to the resin mixed for 12 h. The solution was then drained, washed with DMF (3×) and a mixture of acetic anhydride/pyridine (3:2, 10 mL) was added. The resin was mixed for 15 min to cap the unreacted resin sites. The resin was then washed with DMF (3×). This procedure yielded 0.17 mmol/g of loaded resin.

The Fmoc-AEPA-Rink amide AM resin was subjected to cycles of peptide coupling with Fmoc-protected amino acid building blocks as described above, ending with cleavage of the terminal Fmoc. The resin was then washed with CH$_2$Cl$_2$ (3×) and then dried by pushing N$_2$ gas through the Poly-Prep column. The peptide was cleaved from the resin and globally deprotected by mixing the dried resin with TFA/triisopropylsilane (TIPS)/H$_2$O (18:1:1, 10 mL) and gently rocking for 2.5 hours. The peptide was drained into a glass beaker, precipitated in cold ether, and subjected to purification by RP-HPLC as described above. The synthesis of peptide-1a yielded 17 mg (40.4% yield based on resin loading) of the peptide as the TFA salt.

Synthesis of Peptide-1c.

2-Chlorotrityl chloride resin (300 mg, 1.6 mmol/g) was added to a Bio-Rad Poly-Prep chromatography column (10 mL). The resin was suspended in dry $CH_2Cl_2$ (10 mL) and allowed to swell for 30 min. The solution was drained from the resin and a solution of Fmoc-Gln(Trt)-OH (0.50 equiv, 146.57 mg, 0.24 mmol) in 6% (v/v) 2,4,6-collidine in dry $CH_2Cl_2$ (8 mL) was added immediately and the suspension was gently agitated for 12 h. The solution was then drained and a mixture of $CH_2Cl_2$/MeOH/N,N-diisopropylethylamine (DIPEA) (17:2:1, 10 mL) was added immediately. The mixture was gently agitated for 1 h to cap the unreacted 2-chlorotrityl chloride resin sites. The resin was then washed with dry $CH_2Cl_2$ (2×) and dried by passing nitrogen through the vessel. This procedure yielded 0.36 mmol/g of loaded resin.

The Fmoc-Gln(Trt)-2-chlorotrityl resin was subjected to cycles of peptide coupling with Fmoc-protected amino acid building blocks as described above, ending with cleavage of the terminal Fmoc. The resin was then washed with $CH_2Cl_2$ (3×) and then dried by pushing N2 gas through the Poly-Prep column. The peptide was cleaved from the resin and globally deprotected by mixing the dried resin with TFA/triisopropylsilane (TIPS)/$H_2O$ (18:1:1, 10 mL) and gently rocking for 2.5 hours. The peptide was drained into a glass beaker, precipitated in cold ether, and subjected to purification by RP-HPLC as described above. The synthesis of peptide-1c yielded 13 mg (13.6% yield based on resin loading) of the peptide as the TFA salt.

Synthesis of $H_2$N-K(Dabcyl)-TSAVLQSGFRKM-E(EDANS)-$NH_2$ (SEQ ID NO: 57).

Rink amide AM resin (300 mg, 0.68 mmol/g) was added to a peptide synthesis coupling vessel. The resin was suspended in dry DMF (10 mL) and allowed to swell for 30 min. The solution was drained from the resin and the Fmoc group was removed with 20% (v/v) piperidine in DMF for 20 min. The solution was drained and washed with DMF (5×). Fmoc-Glu(EDANS)-OH (1.5 equiv, 189 mg, 0.306 mmol), HATU (1.5 equiv), and HOAt (1.5 equiv) in 20% (v/v) 2,4,6-collidine in dry DMF (8 mL) was then added to the resin mixed for 12 h. The solution was then drained, washed with DMF (3×) and a mixture of acetic anhydride/pyridine (3:2, 10 mL) was added. The resin was mixed for 15 min to cap the unreacted resin sites. The resin was then washed with DMF (3×). This procedure yielded 0.48 mmol/g of loaded resin.

Fmoc-Glu(EDANS)-Rink amide AM resin was subjected to cycles of peptide coupling with Fmoc-protected amino acid building blocks as described above. For coupling Fmoc-Lys(Dabcyl)-OH, Fmoc-Lys(Dabcyl)-OH (2 equiv, 180.3 mg, 0.408 mmol), HATU (2 equiv), and HOAt (2 equiv) in 20% (v/v) 2,4,6-collidine in dry DMF was added to the resin and mixed for 24 h. The resin was then washed with DMF (3×) and the terminal Fmoc was removed with 20% (v/v) piperidine in DMF for 20 min. The resin was then washed with DMF (3×) followed by $CH_2Cl_2$ (3×) and then dried by pushing N2 gas through the Poly-Prep column. The peptide was cleaved from the resin and globally deprotected by mixing the dried resin with TFA/triisopropylsilane (TIPS)/$H_2O$ (18:1:1, 20 mL) in a round bottom flask and stirring for 2.5 hours. The peptide was drained into a glass beaker, precipitated in cold ether, and subjected to purification by RP-HPLC as described above. The synthesis of $H_2$N-K(Dabcyl)-TSAVLQSGFRKM-E(EDANS)-$NH_2$ (SEQ ID NO: 57) yielded 42 mg (12.6% based on resin loading) of the peptide as the TFA salt.

Enzyme Inhibition Assay.

A proprietary assay buffer containing detergent was used for the inhibition assays (BPS Bioscience, catalog #79956). The substrate with the cleavage site of $M^{pro}$ (indicated by the arrow, ↓), $H_2$N-K(Dabcyl)-TSAVLQ↓SGFRKM-E(EDANS)-$NH_2$ (SEQ. ID No. 57), was used in the fluorescence resonance energy transfer (FRET) based continuous kinetic assay, using a black-walled 96-well plate. The emergence of EDANS fluorescence due to the cleavage of the substrate by $M^{pro}$ was monitored at 460 nm, with excitation at 360 nm, using a Varioskan LUX fluorescence spectrophotometer (Thermo Fisher) using the top-read mode at 37° C. Stock solutions (20 mg/mL) of UCI-1, peptide-1a, and peptide-1b were prepared gravimetrically by dissolving the peptides in deionized $H_2O$ and then diluted in assay buffer to create 10× solutions for each concentration in a serial dilution. For the determination of the $IC_{50}$, 0.1 µM SARS-CoV-2 $M^{pro}$ was incubated with UCI-1, peptide-1a, or peptide-1b at various concentrations (23.4-750 µM for UCI-1 and 187.5-1500 µM for peptide-1a and peptide-1b) in assay buffer at 37° C. for 30 min. Afterward, the reaction was initiated by adding the FRET peptide substrate at a 50 µM final concentration (final well volume: 50 µL). The $IC_{50}$ value for UCI-1 was determined using the GraphPad Prism 8.4.3 software by plotting the initial rates. Measurements of enzymatic activity were performed in triplicate and are presented as the mean±standard deviations (s.d.).

LC/MS Analysis of Enzyme Inhibition Assay Well Solution.

LC/MS analysis of the pooled 187.5 µM UCI-1 well solutions from the enzyme inhibition assay was performed on a Waters Xevo Qtof G2XS equipped with a C4 column. For both LC/MS traces, 5 µL of the well solution (diluted 1:2 in deionized $H_2O$) was injected on the column. For the spiking experiment, a 10 mg/mL stock solution of peptide-1c was prepared gravimetrically in deionized $H_2O$, and an aliquot of the stock solution was diluted in deionized $H_2O$ to create a 1 mM working solution. A 1-µL aliquot of the 1 mM working solution of peptide-1c was added to 100 µL of the well solution to achieve a final peptide-1c concentration of 10 µM.

LDH Release Assay.

The LDH release assay was performed using the Pierce LDH Cytotoxicity Assay Kit from Thermo Scientific. Experiments were performed in replicates of five, and an additional 10 wells were used for controls. Cells were cultured in the inner 60 wells (rows B-G, columns 2-11) of the 96-well plate. DMEM:F12 media (100 µL) was added to the outer wells (rows A and H and columns 1 and 12), in order to ensure the greatest reproducibility of data generated from the inner wells. A 10-mg/mL stock solution of UCI-1 was prepared gravimetrically in sterile deionized $H_2O$ that had been passed through a 0.2 µm nylon syringe filter. The stock solution was used to create a 2560 µM solution of UCI-1, which was serially diluted in sterile deionized $H_2O$ to create 10× working solutions of UCI-1.

HEK-293 cells were plated in a 96-well plate at 15,000 cells per well. Cells were incubated in 100 µL of a 1:1 mixture of DMEM:F12 media supplemented with 10% fetal bovine serum, 100 U/mL penicillin, and 100 µg/mL streptomycin at 37° C. in a 5% $CO_2$ atmosphere and allowed to adhere to the bottom of the plate for 24 hours. After 24 hours, the culture media was removed and replaced with 90 µL of serum-free DMEM:F12 media. A 10-µL aliquot of the working solutions of UCI-1 was added to each well, for well concentrations of 256 µM to 32 µM. Experiments were run in replicates of five. Five wells were used as controls and received 10-µL aliquots of sterile deionized water (vehicle). Another five wells were left untreated, to be subsequently used as controls with lysis buffer for the LDH release assay. Cells were incubated at 37° C. in a 5% $CO_2$ atmosphere for 72 hours.

After 72 hours, 10 µL of 10× lysis buffer—included with the assay kit—was added to the five untreated wells, and the cells were incubated for an additional 45 min. After 45 min, a 50-µL aliquot of the supernatant media from each well was transferred to a new 96-well plate and 50 µL of LDH substrate solution, prepared according to manufacturer's protocol, was added to each well. The treated plates were stored in the dark for 30 min. The absorbance of each well was measured at 490 and 680 nm ($A_{490}$ and $A_{680}$). Data were processed by calculating the differential absorbance for each well ($A_{490}-A_{680}$) and comparing those values to those of the lysis buffer controls and the untreated controls:

% cell death=$[(A_{490}-A_{680})_{compound}-(A_{490}-A_{680})_{vehicle}]/[(A_{490}-A_{680})_{lysis}-(A_{490}-A_{680})_{vehicle}]$ Docking of UCI-1 to SARS-COV-2 $M^{pro}$.

The model of the SARS-CoV-2 $M^{pro}$ was generated as follows: Starting coordinates of SARS-CoV-2 $M^{pro}$ were generated from the SARS-CoV-2 $M^{pro}$ crystallographic structure (PDB 6YB7) using PyMOL and were saved as a new PDB file. In PyMOL, the dimethyl sulfoxide molecule that sits in the active site of 6YB7 was deleted. A minimum energy (global minimum) structure of UCI-1 was generated by conformational searching in MacroModel (MMFFs force field in GB/SA water). iBabel was used to convert the PDB file generated in MacroModel into a PDBQT file prior to docking. Docking was performed using AutoDock Tools and AutoDock Vina. In AutoDock Tools, a grid was chosen to encompass the active site of SARS-CoV-2 $M^{pro}$ in the size of 25×25×25 Å and with the coordinates x=9.250, y=−5.944, z=18.944. SARS CoV-2 $M^{pro}$ was treated as a rigid receptor in these calculations. The lowest energy cluster, as determined by AutoDock Vina, was chosen to represent the docking model shown in FIG. 7C.

Molecular Dynamics Simulation.

The initial SARS-CoV-2 $M^{pro}$ model that was used for MD simulations was generated from the final frame of the published wild type $M^{pro}$ trajectory, which was originally seeded with PDB structure 6Y2E. Initial peptide conformations were obtained by docking UCI-1, peptide-1a, and peptide-1b respectively to the A chain active site of the initial $M^{pro}$ model using AutoDock Vina; the search box in each case was given a radius equal to 10 times the peptide's radius of gyration, centered on residue M165 (chosen because of its central location in the conserved substrate binding region, as confirmed by both visual inspection of the structure and the analysis of Z. Jin et al., Nature. 2020; 582:289-293, the disclosure of which is incorporated herein by reference), and an exhaustiveness of 32 was employed. Out of the 25 minimum energy poses, the pose most closely resembling the conformation found when docking against PDB 6YB7 was retained for use as the initial condition. CHARMM representations of the peptide models were created using CGenFF version 3.01 (K. Vanommeslaeghe and A. D. Mackerrel Jr., J Chem Inf Model. 2012; 52:3144-54; and K. Vanommeslaeghe, E. P. Raman, and A. D. MacKerell Jr., J Chem Inf Model. 2012; 52:3155-68; the disclosure of which are each incorporated herein by reference). The combined peptide/dimer structures were solvated in TIP3P water using VMD version 1.9.3 (W. Humphrey, A. Dalke, and K. Schulten, J Mol Graph. 1996; 1433-8, 27-8, the disclosure of which is incorporated herein by reference); a cubic water box with minimum margin of 10 Å from the protein complex on each side was employed, with NaCl added to achieve neutral charge. Each complex was subsequently minimized for 10,000 iterations using namd 2.13 with the CHARMM 36m force field (J. C. Phillips, et al., J Comput Chem. 2005; 26:1781-802; and J. Huang, et al., Nat Methods. 2017 January; 14(1):71-73; the disclosures of which are each incorporated herein by reference), followed by a 10 ps simulation period for box adjustment. (All simulations were performed using periodic boundary conditions with an NpT ensemble at 310K and 1 atm, Langevin dynamics with a damping coefficient of 1/ps and a Nose-Hoover Langevin piston were respectively employed for temperature and pressure control (G. J. Martyna, D. J. Tobias, and M. L. Klein, J. Chem. Phys. 1994; 101:4177-4189; and S. E. Feller, et el. J. Chem. Phys. 1995; 103:4613-4621, the disclosures of which are each herein incorporated by reference). Rigid bonds were used only for water molecules, and a 1 fs step size was employed.) Following adjustment, each complex was simulated for 10 ns, with 1,000 frames being retained for subsequent analysis (1/ps). Visualization and analysis of the resulting trajectories was performed with VMD.

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:

1. A compound of formula

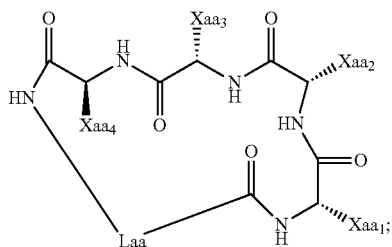

wherein:

Xaa₁ is a hydrophobic amino acid;

Xaa₂ is an amino acid capable of hydrogen bonding;

Xaa₃ is any amino acid;

Xaa₄ is any amino acid; and

Laa is a linker amino acid, wherein the linker amino acid is [3-(2-aminoethyl)phenyl]-acetic acid, [4-(2-aminoethyl)phenyl]-acetic acid, 2-(5-(2-aminoethyl)furan-2-yl)acetic acid, 2-(5-(2-aminoethyl)thiophen-2-yl)acetic acid, 2-(5-(2-aminoethyl)-1H-pyrrol-2-yl)acetic acid, 6-aminohexanoic acid, 7-aminoheptanoic acid, 8-aminooctanoic acid, or 9-aminononanoic acid.

2. The compound of claim 1, wherein:

Xaa₁ is Phe, d-Phe, homo-Phe, Leu, d-Leu, or Cha;

Xaa₂ is Gln or γ-lactam Gln;

Xaa₃ is Gly, Ser, Ala, Asn, Phe, Trp, phenylglycine Thr, or allo-Thr; and

Xaa₄ is Lys, Gly, Ala, Val, or Leu.

3. The compound of claim 1, wherein the Xaa₁ is Phe, d-Phe, or homo-Phe and the aromatic ring incorporates at least one substituent, the substituent being $CH_3$, $CH_2CH_3$, $CH_2(CH_3)_2$, phenyl, benzoyl, pyridyl, acetyl, or a halogen.

4. The compound of claim 1, wherein the Xaa₁ is

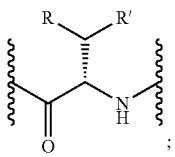

wherein R is H, $CH_3$, $CH_2CH_3$, $CH_2(CH_3)_2$, $(CH_3)_2$, $(CH_3)_3$, or cyclopropyl; and wherein R' is H, $CH_3$, $CH_2CH_3$, $CH_2(CH_3)_2$, $(CH_3)_2$, $(CH_3)_3$, or cyclopropyl.

5. The compound of claim 1, wherein the linker amino acid is 4-(2-aminoethyl)phenyl]-acetic acid and is optionally substituted as follows:

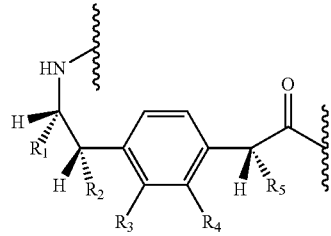

wherein each of $R_1$, $R_2$, $R_3$, $R_4$, and $R_5$ is H or $CH_3$.

6. The compound of claim 1, wherein the sequence of Xaa₁, Xaa₂, Xaa₃, and Xaa₄ is selected from the group consisting of SEQ. ID. Nos. SEQ ID NOs: 2 to 55.

7. The compound of claim 6, wherein the sequence of Xaa₁, Xaa₂, Xaa₃, and Xaa₄ consists of SEQ ID NO: 55.

8. The compound of claim 6, wherein the sequence of Xaa₁, Xaa₂, Xaa₃, and Xaa₄ consists of SEQ ID NO: 2.

9. A cyclic peptide comprising:

five to fifty amino acids, wherein the cyclic peptide comprises an amino acid linker that provides linker function between the amino group of a first amino acid and the carboxyl group of the penultimate amino acid, wherein the penultimate amino acid is the amino acid linker; wherein the cyclic peptide has the following formula:

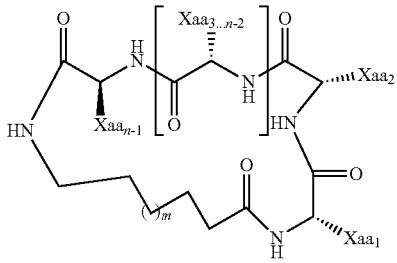

wherein each Xaa is an amino acid side chain, n is 5 to 50, and m is 1 to 4.

10. The cyclic peptide of claim 9, wherein the amino acid linker comprises a planar cyclic group.

11. The cyclic peptide of claim 9, wherein the amino acid linker comprises five or six atoms in a single plane.

12. The cyclic peptide of claim 9, wherein the amino acid linker is [4-(2-aminoethyl)phenyl]-acetic acid or [3-(2-aminoethyl)phenyl]-acetic acid.

13. The cyclic peptide of claim 9, wherein the amino acid linker is 2-(5-(2-aminoethyl)furan-2-yl)acetic acid, 2-(5-(2-aminoethyl)thiophen-2-yl)acetic acid, or 2-(5-(2-aminoethyl)-1H-pyrrol-2-yl)acetic acid.

14. The cyclic peptide of claim 9 having the following formula:

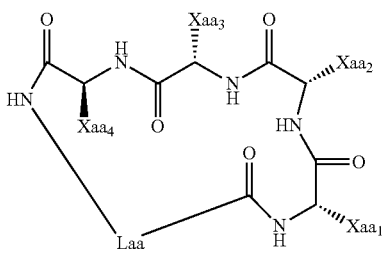

wherein: Xaa₁, Xaa₂, Xaa₃, and Xaa₄ are each any amino acid and Laa is the linker amino acid.

15. A method of prevention and/or treatment for coronavirus, comprising:
administering to a subject an effective amount of a compound of formula

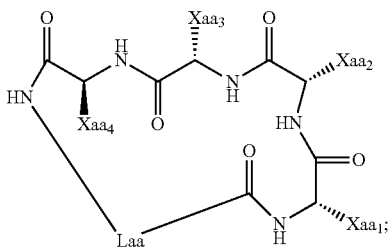

$Xaa_1$ is a hydrophobic amino acid;
$Xaa_2$ is an amino acid capable of hydrogen bonding;
$Xaa_3$ is any amino acid;
$Xaa_4$ is any amino acid; and
Laa is a linker amino acid, wherein the linker amino acid is [3-(2-aminoethyl)phenyl]-acetic acid, [4-(2-aminoethyl)phenyl]-acetic acid, 2-(5-(2-aminoethyl)furan-2-yl)acetic acid, 2-(5-(2-aminoethyl)thiophen-2-yl)acetic acid, 2-(5-(2-aminoethyl)-1H-pyrrol-2-yl)acetic acid, 6-aminohexanoic acid, 7-aminoheptanoic acid, 8-aminooctanoic acid, or 9-aminononanoic acid.

16. The method of claim 15, wherein:
wherein:
$Xaa_1$ is Phe, d-Phe, homo-Phe, Leu, d-Leu, or Cha;
$Xaa_2$ is Gln or γ-lactam Gln;
$Xaa_3$ is Gly, Ser, Ala, Asn, Phe, Trp, phenylglycine Thr, or allo-Thr; and
$Xaa_4$ is Lys, Gly, Ala, Val, or Leu.

17. The method of claim 15, wherein the $Xaa_1$ is Phe, d-Phe, or homo-Phe and the aromatic ring incorporates at least one substituent, the substituent being $CH_3$, $CH_2CH_3$, $CH_2(CH_3)_2$, phenyl, benzoyl, pyridyl, acetyl, or a halogen.

18. The method of claim 15, wherein the $Xaa_1$ is

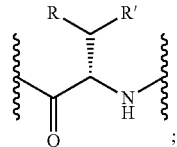

wherein R is H, $CH_3$, $CH_2CH_3$, $CH_2(CH_3)_2$, $(CH_3)_2$, $(CH_3)_3$, or cyclopropyl; and wherein R' is H, $CH_3$, $CH_2CH_3$, $CH_2(CH_3)_2$, $(CH_3)_2$, $(CH_3)_3$, or cyclopropyl.

19. The method of claim 15, wherein the linker amino acid is 4-(2-aminoethyl)phenyl]-acetic acid and is optionally substituted as follows:

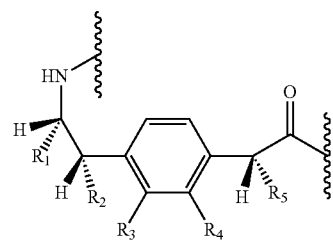

wherein each of $R_1$, $R_2$, $R_3$, $R_4$, and $R_5$ is H or $CH_3$.

20. The method of claim 15, wherein the sequence of $Xaa_1$, $Xaa_2$, $Xaa_3$, and $Xaa_4$ is selected from the group consisting of SEQ ID NOs:2 to 55.

21. The method of claim 20, wherein the sequence of $Xaa_1$, $Xaa_2$, $Xaa_3$, and $Xaa_4$ consists of SEQ ID NO: 55.

22. The method of claim 20, wherein the sequence of $Xaa_1$, $Xaa_2$, $Xaa_3$, and $Xaa_4$ consists of SEQ ID NO: 2.

23. The method of claim 15, wherein the subject is infected with coronavirus.

24. The method of claim 15, wherein administering the compound to the subject is to prophylactically treat an infection of coronavirus.

25. The method of claim 15, wherein the subject is a human, a pet, a farm animal, or a zoo animal.

* * * * *

SEQUENCE LISTING

<160> NUMBER OF SEQ ID NOS: 61

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 1

Phe Gln Gly Lys Phe
1               5

```
<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Gln Ser Lys
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys, Gly, Ala, Val or Leu

<400> SEQUENCE: 3

Phe Gln Ser Xaa
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 4

Phe Gln Ser Xaa
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly, Ser, Ala, Asn, Phe, Trp, phenylglycine Thr
      or allo-Thr

<400> SEQUENCE: 5

Phe Gln Xaa Lys
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (3)..(3)
<223> OTHER INFORMATION: Gly, Ser, Ala, Asn, Phe, Trp, phenylglycine Thr
      or allo-Thr
<220> FEATURE:
<221> NAME/KEY: MOD_RES
<222> LOCATION: (4)..(4)
<223> OTHER INFORMATION: Lys, Gly, Ala, Val or Leu

<400> SEQUENCE: 6

Phe Gln Xaa Xaa
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly, Ser, Ala, Asn, Phe, Trp, phenylglycine Thr
      or allo-Thr
<220> FEATURE:
<221> NAME/KEY: MOD_RES
<222> LOCATION: (4)..(4)
<223> OTHER INFORMATION: Any amino acid

<400> SEQUENCE: 7

Phe Gln Xaa Xaa
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 8

Phe Gln Xaa Lys
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Lys, Gly, Ala, Val or Leu

<400> SEQUENCE: 9

Phe Gln Xaa Xaa
1

<210> SEQ ID NO 10
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 10

Phe Gln Xaa Xaa
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gamma-lactam Gln

<400> SEQUENCE: 11

Phe Gln Ser Lys
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gamma-lactam Gln
<220> FEATURE:
<221> NAME/KEY: MOD_RES
<222> LOCATION: (4)..(4)
<223> OTHER INFORMATION: Lys, Gly, Ala, Val or Leu

<400> SEQUENCE: 12

Phe Gln Ser Xaa
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gamma-lactam Gln
<220> FEATURE:
<221> NAME/KEY: MOD_RES
<222> LOCATION: (4)..(4)
<223> OTHER INFORMATION: Any amino acid

<400> SEQUENCE: 13
```

Phe Gln Ser Xaa
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gamma-lactam Gln
<220> FEATURE:
<221> NAME/KEY: MOD_RES
<222> LOCATION: (3)..(3)
<223> OTHER INFORMATION: Gly, Ser, Ala, Asn, Phe, Trp, phenylglycine Thr
      or allo-Thr

<400> SEQUENCE: 14

Phe Gln Xaa Lys
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gamma-lactam Gln
<220> FEATURE:
<221> NAME/KEY: MOD_RES
<222> LOCATION: (3)..(3)
<223> OTHER INFORMATION: Gly, Ser, Ala, Asn, Phe, Trp, phenylglycine Thr
      or allo-Thr
<220> FEATURE:
<221> NAME/KEY: MOD_RES
<222> LOCATION: (4)..(4)
<223> OTHER INFORMATION: Lys, Gly, Ala, Val or Leu

<400> SEQUENCE: 15

Phe Gln Xaa Xaa
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gamma-lactam Gln
<220> FEATURE:
<221> NAME/KEY: MOD_RES
<222> LOCATION: (3)..(3)
<223> OTHER INFORMATION: Gly, Ser, Ala, Asn, Phe, Trp, phenylglycine Thr
      or allo-Thr
<220> FEATURE:
<221> NAME/KEY: MOD_RES
<222> LOCATION: (4)..(4)
<223> OTHER INFORMATION: Any amino acid

<400> SEQUENCE: 16

Phe Gln Xaa Xaa
1

```
<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gamma-lactam Gln
<220> FEATURE:
<221> NAME/KEY: MOD_RES
<222> LOCATION: (3)..(3)
<223> OTHER INFORMATION: Any amino acid

<400> SEQUENCE: 17

Phe Gln Xaa Lys
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gamma-lactam Gln
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Lys, Gly, Ala, Val or Leu

<400> SEQUENCE: 18

Phe Gln Xaa Xaa
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gamma-lactam Gln
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 19

Phe Gln Xaa Xaa
1

<210> SEQ ID NO 20
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln, Gamma-lactam Gln or D-Gln

<400> SEQUENCE: 20

Phe Xaa Ser Lys
1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln, Gamma-lactam Gln or D-Gln
<220> FEATURE:
<221> NAME/KEY: MOD_RES
<222> LOCATION: (4)..(4)
<223> OTHER INFORMATION: Lys, Gly, Ala, Val or Leu

<400> SEQUENCE: 21

Phe Xaa Ser Xaa
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln, Gamma-lactam Gln or D-Gln
<220> FEATURE:
<221> NAME/KEY: MOD_RES
<222> LOCATION: (4)..(4)
<223> OTHER INFORMATION: Any amino acid

<400> SEQUENCE: 22

Phe Xaa Ser Xaa
1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln, Gamma-lactam Gln or D-Gln
<220> FEATURE:
<221> NAME/KEY: MOD_RES
<222> LOCATION: (3)..(3)
<223> OTHER INFORMATION: Gly, Ser, Ala, Asn, Phe, Trp, phenylglycine Thr
      or allo-Thr

<400> SEQUENCE: 23

Phe Xaa Xaa Lys
```

```
<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln, Gamma-lactam Gln or D-Gln
<220> FEATURE:
<221> NAME/KEY: MOD_RES
<222> LOCATION: (3)..(3)
<223> OTHER INFORMATION: Gly, Ser, Ala, Asn, Phe, Trp, phenylglycine Thr
      or allo-Thr
<220> FEATURE:
<221> NAME/KEY: MOD_RES
<222> LOCATION: (4)..(4)
<223> OTHER INFORMATION: Lys, Gly, Ala, Val or Leu

<400> SEQUENCE: 24

Phe Xaa Xaa Xaa
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln, Gamma-lactam Gln or D-Gln
<220> FEATURE:
<221> NAME/KEY: MOD_RES
<222> LOCATION: (3)..(3)
<223> OTHER INFORMATION: Gly, Ser, Ala, Asn, Phe, Trp, phenylglycine Thr
      or allo-Thr
<220> FEATURE:
<221> NAME/KEY: MOD_RES
<222> LOCATION: (4)..(4)
<223> OTHER INFORMATION: Any amino acid

<400> SEQUENCE: 25

Phe Xaa Xaa Xaa
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln, Gamma-lactam Gln or D-Gln
<220> FEATURE:
<221> NAME/KEY: MOD_RES
<222> LOCATION: (3)..(3)
<223> OTHER INFORMATION: Any amino acid

<400> SEQUENCE: 26

Phe Xaa Xaa Lys
1
```

-continued

```
<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln, Gamma-lactam Gln or D-Gln
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Lys, Gly, Ala, Val or Leu

<400> SEQUENCE: 27

Phe Xaa Xaa Xaa
1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln, Gamma-lactam Gln or D-Gln
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 28

Phe Xaa Xaa Xaa
1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha

<400> SEQUENCE: 29

Xaa Gln Ser Lys
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (4)..(4)
<223> OTHER INFORMATION: Lys, Gly, Ala, Val or Leu

<400> SEQUENCE: 30

Xaa Gln Ser Xaa
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (4)..(4)
<223> OTHER INFORMATION: Any amino acid

<400> SEQUENCE: 31

Xaa Gln Ser Xaa
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (3)..(3)
<223> OTHER INFORMATION: Gly, Ser, Ala, Asn, Phe, Trp, phenylglycine Thr
      or allo-Thr

<400> SEQUENCE: 32

Xaa Gln Xaa Lys
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (3)..(3)
<223> OTHER INFORMATION: Gly, Ser, Ala, Asn, Phe, Trp, phenylglycine Thr
      or allo-Thr
<220> FEATURE:
<221> NAME/KEY: MOD_RES
<222> LOCATION: (4)..(4)
<223> OTHER INFORMATION: Lys, Gly, Ala, Val or Leu
```

```
<400> SEQUENCE: 33

Xaa Gln Xaa Xaa
1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (3)..(3)
<223> OTHER INFORMATION: Gly, Ser, Ala, Asn, Phe, Trp, phenylglycine Thr
      or allo-Thr
<220> FEATURE:
<221> NAME/KEY: MOD_RES
<222> LOCATION: (4)..(4)
<223> OTHER INFORMATION: Any amino acid

<400> SEQUENCE: 34

Xaa Gln Xaa Xaa
1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (3)..(3)
<223> OTHER INFORMATION: Any amino acid

<400> SEQUENCE: 35

Xaa Gln Xaa Lys
1

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Lys, Gly, Ala, Val or Leu

<400> SEQUENCE: 36

Xaa Gln Xaa Xaa
1
```

```
<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 37

Xaa Gln Xaa Xaa
1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (2)..(2)
<223> OTHER INFORMATION: Gamma-lactam Gln

<400> SEQUENCE: 38

Xaa Gln Ser Lys
1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (2)..(2)
<223> OTHER INFORMATION: Gamma-lactam Gln
<220> FEATURE:
<221> NAME/KEY: MOD_RES
<222> LOCATION: (4)..(4)
<223> OTHER INFORMATION: Lys, Gly, Ala, Val or Leu

<400> SEQUENCE: 39

Xaa Gln Ser Xaa
1

<210> SEQ ID NO 40
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (2)..(2)
<223> OTHER INFORMATION: Gamma-lactam Gln
<220> FEATURE:
<221> NAME/KEY: MOD_RES
<222> LOCATION: (4)..(4)
<223> OTHER INFORMATION: Any amino acid

<400> SEQUENCE: 40

Xaa Gln Ser Xaa
1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (2)..(2)
<223> OTHER INFORMATION: Gamma-lactam Gln
<220> FEATURE:
<221> NAME/KEY: MOD_RES
<222> LOCATION: (3)..(3)
<223> OTHER INFORMATION: Gly, Ser, Ala, Asn, Phe, Trp, phenylglycine Thr
      or allo-Thr

<400> SEQUENCE: 41

Xaa Gln Xaa Lys
1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (2)..(2)
<223> OTHER INFORMATION: Gamma-lactam Gln
<220> FEATURE:
<221> NAME/KEY: MOD_RES
<222> LOCATION: (3)..(3)
<223> OTHER INFORMATION: Gly, Ser, Ala, Asn, Phe, Trp, phenylglycine Thr
      or allo-Thr
<220> FEATURE:
<221> NAME/KEY: MOD_RES
<222> LOCATION: (4)..(4)
<223> OTHER INFORMATION: Lys, Gly, Ala, Val or Leu

<400> SEQUENCE: 42

Xaa Gln Xaa Xaa
1
```

```
<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (2)..(2)
<223> OTHER INFORMATION: Gamma-lactam Gln
<220> FEATURE:
<221> NAME/KEY: MOD_RES
<222> LOCATION: (3)..(3)
<223> OTHER INFORMATION: Gly, Ser, Ala, Asn, Phe, Trp, phenylglycine Thr
      or allo-Thr
<220> FEATURE:
<221> NAME/KEY: MOD_RES
<222> LOCATION: (4)..(4)
<223> OTHER INFORMATION: Any amino acid

<400> SEQUENCE: 43

Xaa Gln Xaa Xaa
1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (2)..(2)
<223> OTHER INFORMATION: Gamma-lactam Gln
<220> FEATURE:
<221> NAME/KEY: MOD_RES
<222> LOCATION: (3)..(3)
<223> OTHER INFORMATION: Any amino acid

<400> SEQUENCE: 44

Xaa Gln Xaa Lys
1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (2)..(2)
<223> OTHER INFORMATION: Gamma-lactam Gln
<220> FEATURE:
<221> NAME/KEY: MOD_RES
<222> LOCATION: (3)..(3)
<223> OTHER INFORMATION: Any amino acid
<220> FEATURE:
```

```
<221> NAME/KEY: MOD_RES
<222> LOCATION: (4)..(4)
<223> OTHER INFORMATION: Lys, Gly, Ala, Val or Leu

<400> SEQUENCE: 45

Xaa Gln Xaa Xaa
1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (2)..(2)
<223> OTHER INFORMATION: Gamma-lactam Gln
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 46

Xaa Gln Xaa Xaa
1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (2)..(2)
<223> OTHER INFORMATION: Gln, Gamma-lactam Gln or D-Gln

<400> SEQUENCE: 47

Xaa Xaa Ser Lys
1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (2)..(2)
<223> OTHER INFORMATION: Gln, Gamma-lactam Gln or D-Gln
<220> FEATURE:
<221> NAME/KEY: MOD_RES
```

```
<222> LOCATION: (4)..(4)
<223> OTHER INFORMATION: Lys, Gly, Ala, Val or Leu

<400> SEQUENCE: 48

Xaa Xaa Ser Xaa
1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (2)..(2)
<223> OTHER INFORMATION: Gln, Gamma-lactam Gln or D-Gln
<220> FEATURE:
<221> NAME/KEY: MOD_RES
<222> LOCATION: (4)..(4)
<223> OTHER INFORMATION: Any amino acid

<400> SEQUENCE: 49

Xaa Xaa Ser Xaa
1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (2)..(2)
<223> OTHER INFORMATION: Gln, Gamma-lactam Gln or D-Gln
<220> FEATURE:
<221> NAME/KEY: MOD_RES
<222> LOCATION: (3)..(3)
<223> OTHER INFORMATION: Gly, Ser, Ala, Asn, Phe, Trp, phenylglycine Thr
      or allo-Thr

<400> SEQUENCE: 50

Xaa Xaa Xaa Lys
1

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (2)..(2)
<223> OTHER INFORMATION: Gln, Gamma-lactam Gln or D-Gln
<220> FEATURE:
<221> NAME/KEY: MOD_RES
```

```
<222> LOCATION: (3)..(3)
<223> OTHER INFORMATION: Gly, Ser, Ala, Asn, Phe, Trp, phenylglycine Thr
      or allo-Thr
<220> FEATURE:
<221> NAME/KEY: MOD_RES
<222> LOCATION: (4)..(4)
<223> OTHER INFORMATION: Lys, Gly, Ala, Val or Leu

<400> SEQUENCE: 51

Xaa Xaa Xaa Xaa
1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (2)..(2)
<223> OTHER INFORMATION: Gln, Gamma-lactam Gln or D-Gln
<220> FEATURE:
<221> NAME/KEY: MOD_RES
<222> LOCATION: (3)..(3)
<223> OTHER INFORMATION: Gly, Ser, Ala, Asn, Phe, Trp, phenylglycine Thr
      or allo-Thr
<220> FEATURE:
<221> NAME/KEY: MOD_RES
<222> LOCATION: (4)..(4)
<223> OTHER INFORMATION: Any amino acid

<400> SEQUENCE: 52

Xaa Xaa Xaa Xaa
1

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (2)..(2)
<223> OTHER INFORMATION: Gln, Gamma-lactam Gln or D-Gln
<220> FEATURE:
<221> NAME/KEY: MOD_RES
<222> LOCATION: (3)..(3)
<223> OTHER INFORMATION: Any amino acid

<400> SEQUENCE: 53

Xaa Xaa Xaa Lys
1

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (2)..(2)
<223> OTHER INFORMATION: Gln, Gamma-lactam Gln or D-Gln
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Lys, Gly, Ala, Val or Leu

<400> SEQUENCE: 54

Xaa Xaa Xaa Xaa
1

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, D-Phe, homo-Phe, Leu, d-Leu or Cha
<220> FEATURE:
<221> NAME/KEY: MOD_RES
<222> LOCATION: (2)..(2)
<223> OTHER INFORMATION: Gln, Gamma-lactam Gln or D-Gln
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 55

Xaa Xaa Xaa Xaa
1

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Gly Val Thr Phe Gln Gly Lys Phe Lys
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Thr Ser Ala Val Leu Gln Ser Gly Phe Arg Lys Met Glu
1               5                   10
```

```
<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: [4-(2-aminoethyl)phenyl]-acetic acid

<400> SEQUENCE: 58

Phe Gln Ser Lys Xaa
1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [4-(2-aminoethyl)phenyl]-acetic acid

<400> SEQUENCE: 59

Xaa Phe Gln Ser Lys Phe
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln(Trt)
<220> FEATURE:
<221> NAME/KEY: MOD_RES
<222> LOCATION: (3)..(3)
<223> OTHER INFORMATION: Ser(tBu)
<220> FEATURE:
<221> NAME/KEY: MOD_RES
<222> LOCATION: (4)..(4)
<223> OTHER INFORMATION: Lys(Boc)
<220> FEATURE:
<221> NAME/KEY: MOD_RES
<222> LOCATION: (5)..(5)
<223> OTHER INFORMATION: [4-(2-aminoethyl)phenyl]-acetic acid

<400> SEQUENCE: 60

Phe Gln Ser Lys Xaa
1               5

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [4-(2-aminoethyl)phenyl]-acetic acid
```

```
<400> SEQUENCE: 61

Xaa Phe Gln Ser
1
```